US011607163B2

(12) United States Patent
Iyer et al.

(10) Patent No.: US 11,607,163 B2
(45) Date of Patent: Mar. 21, 2023

(54) RECHARGEABLE CARDIAC MONITOR DEVICE

(71) Applicant: Medtronic, Inc., Minneapolis, MN (US)

(72) Inventors: Rajesh V. Iyer, Eden Prairie, MN (US); Gordon O. Munns, Stacy, MN (US); Andrew J. Ries, Lino Lakes, MN (US); Craig L. Schmidt, Eagan, MN (US); Paul B. Young, New Richmond, WI (US)

(73) Assignee: Medtronic Inc., Minneapolis, MN (US)

( * ) Notice: Subject to any disclaimer, the term of this patent is extended or adjusted under 35 U.S.C. 154(b) by 501 days.

(21) Appl. No.: 16/743,460

(22) Filed: Jan. 15, 2020

(65) Prior Publication Data

US 2021/0212586 A1    Jul. 15, 2021

(51) Int. Cl.
*A61B 5/283* (2021.01)
*H02J 50/10* (2016.01)
(Continued)

(52) U.S. Cl.
CPC ............ *A61B 5/283* (2021.01); *A61B 5/0031* (2013.01); *H01F 38/14* (2013.01); *H02J 7/02* (2013.01);
(Continued)

(58) Field of Classification Search
CPC ...... A61N 1/375; A61N 1/3758; A61N 1/378; A61N 1/3787; A61N 1/3968;
(Continued)

(56) References Cited

U.S. PATENT DOCUMENTS 6,505,077 B1    1/2003 Kast et al.
7,813,801 B2    10/2010 Youker et al.
(Continued)

FOREIGN PATENT DOCUMENTS

AU    2004281639 B2    4/2005
EP       1598092 B2    11/2005
(Continued)

OTHER PUBLICATIONS

International Search Report and Written Opinion of International Application No. PCT/US2020/064774, dated Apr. 9, 2021, 9 pp.
(Continued)

*Primary Examiner* — Tammie K Marlen
(74) *Attorney, Agent, or Firm* — Shumaker & Sieffert, P.A.

(57) ABSTRACT

Systems, devices and methods allow inductive recharging of a power source located within or coupled to an implantable medical device (IMD) while the device is implanted in a patient. The IMD may include a rechargeable battery having a battery housing; a non-metallic substrate attached to the battery housing, wherein the non-metallic substrate and the battery housing form an outer housing of the implantable medical device; control circuitry formed on the non-metallic substrate within the outer housing of the IMD; a receive coil within the outer housing of the IMD, the receive coil configured to receive energy from outside of the outer housing of the IMD; and recharge circuitry within the outer housing of the IMD and coupled to the receive coil, the recharge circuitry configured to receive the energy from the receive coil, and recharge the rechargeable battery using the received energy.

19 Claims, 14 Drawing Sheets

(51) Int. Cl.
H02J 50/40 (2016.01)
A61B 5/00 (2006.01)
H01F 38/14 (2006.01)
H02J 7/02 (2016.01)

(52) U.S. Cl.
CPC .............. *H02J 50/10* (2016.02); *H02J 50/40* (2016.02); *A61B 2560/0214* (2013.01); *A61B 2562/12* (2013.01)

(58) Field of Classification Search
CPC .... A61B 2560/0214; A61B 2560/0219; A61B 2560/0209; A61B 2562/12; H02J 50/10; H02J 50/40; H01F 38/14
See application file for complete search history.

(56) References Cited

U.S. PATENT DOCUMENTS

| | | |
|---|---|---|
| 8,498,716 B2 | 7/2013 | Chen et al. |
| 9,020,602 B2 | 4/2015 | Aghassian |
| 10,355,512 B2 | 7/2019 | Cinbis et al. |
| 2012/0119698 A1 | 5/2012 | Karalis et al. |
| 2015/0073247 A1 | 3/2015 | Gordon et al. |
| 2017/0025888 A1* | 1/2017 | Cinbis .................... H02J 7/025 |
| 2018/0212451 A1 | 7/2018 | Schmidt et al. |
| 2020/0001095 A1* | 1/2020 | Iyer .................... A61N 1/37229 |

FOREIGN PATENT DOCUMENTS

| | | |
|---|---|---|
| WO | 2012/033752 A1 | 3/2012 |
| WO | 2020/006334 A1 | 1/2020 |

OTHER PUBLICATIONS

"Evaluating Compliance with FCC Guidelines for Human Exposure to Radiofrequency Electromagnetic Fields," Federal Communications Commission Office of Engineering & Technology, Supplement C, Jun. 2001, 57 pp.

"IEEE Standard for Safety Levels with Respect to Human Exposure to Radio Frequency Electromagnetic Fields, 3 KHz to 300 GHz," IEEE-SA Standards Board, Apr. 16, 1999, 83 pp.

Ahn et al., "Optimal Design of Wireless Power Transmission Links for Millimeter-Sized Biomedical Implants," IEEE Transactions on Biomedical Circuits and Systems, vol. 10, No. I, Feb. 2016, 13 pp.

Detroye et al., "The Calculation and Measurement of Helmholtz Coil Fields," Army Research Laboratory, AD-A286 081, Nov. 1994, 20 pp.

Ettorre et al., "A Transponder-Based, Nonradiative Wireless Power Transfer," IEEE Antennas and Wireless Propagation Letters, vol. 11, Sep. 21, 2012, 4 pp.

Gaddam, "Remote power delivery for hybrid integrated Bioimplantable Electrical Stimulation System," Louisiana State University, May 2005, 108 pp.

Grandi et al., "Stray Capacitances of Single-Layer Solenoid Air-Core Inductors," IEEE Transactions on Industry Applications, vol. 35, No. 5, Sep./Oct. 1999, 8 pp.

Jia et al., "The optimization of wireless power transmission: design and realization," The International Journal of Medical Robotics and Computer Assisted Surgery, Wiley Online Library, Apr. 17, 2012, 11 pp.

Kim et al., "Wireless power transfer to a cardiac implant," Applied Physics Letters, published online by American nstitute of Physics Aug. 13, 2012, 5 pp.

Ramrakhyani et al., "Design and Optimization of Resonance-Based Efficient Wireless Power Delivery Systems for Biomedical Implants," IEEE Transactions on Biomedical Circuits and Systems, vol. 5, No. 1, Feb. 2011, 16 pp.

Stevens et al., "Procedure to Calculate the Inductance of a Circular Loop Near a Metal Plate," Electrical Review, ISSN 0033-2097, 2011, 4 pp. (Applicant points out, in accordance with MPEP 609.04 (a), that the year of publication, 2011, is sufficiently earlier than the effective U.S. filing date, so that the particular month of publication is not in issue.).

Wang et al., "Design and Analysis of an Adaptive Transcutaneous Power Telemetry for Biomedical Implants," IEEE Transactions on Circuits and Sytems—I: Regular Papers, vol. 52, No. 10, Oct. 2005, 9 pp.

Wikipedia, "File: Helmholtz coils," accessed from https://commons.wikimedia.org/w/index.php?curid=193184 on or about Dec. 4, 2019, last edit Mar. 17, 2018, 5 pp.

Wikipedia, "Two-port network," accessed from https://en.wikipedia.org/wiki/Two-port_network on or about Dec. 5, 2019, last edit Aug. 31, 2019, 10 pp.

U.S. Appl. No. 16/021,067, filed Jun. 28, 2018, naming inventors Iyer et al.

U.S. Appl. No. 16/021,075, filed Jun. 28, 2018, naming inventors Iyer et al.

* cited by examiner

SECTION B-B

RECHARGEABLE CARDIAC MONITOR DEVICE

TECHNICAL FIELD

The disclosure relates to implantable medical devices and, more particularly, implantable medical devices having rechargeable power sources.

BACKGROUND

Various implantable medical devices (IMDs) have been clinically implanted or proposed for therapeutically treating or monitoring one or more physiological and/or neurological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, implantable loop recorders, and pressure sensors, among others. Such devices may be associated with leads that position electrodes or sensors at a desired location, or may be leadless with electrodes integrated into the device housing. These devices may have the ability to wirelessly transmit data either to another device implanted in the patient or to another instrument located externally of the patient, or both.

Although implantation of some devices requires a surgical procedure (e.g., pacemakers, defibrillators, etc.), other devices may be small enough to be delivered and placed at an intended implant location in a relatively noninvasive manner, such as by a percutaneous delivery catheter, transvenously, or using a subcutaneous delivery tool. As one example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions.

SUMMARY

The disclosure describes implantable medical devices, including receive coil configurations for implantable medical devices and associated techniques, structures, and assemblies configured to provide recharging of power sources located within medical devices that have been implanted within a patient. An implantable medical device (IMD) may include a receive coil (also referred to as a secondary coil) positioned within a portion of the housing of the device. The receive coil may be coupled to recharging circuitry and configured to have currents induced thereon to provide a recharging current for recharging a power source of the IMD. The receive coil may be made from one or more windings formed from individual electrical conductors, such as multi-strand wires. Receive coil configurations include flat spiral-wound coils and tubular coils, as examples. Receive coil configurations as described herein may provide a desired form factor and adequate charge efficiency for an IMD.

In some examples, the receive coil may have a curved shape corresponding to an inner surface of the housing of a portion of the IMD. The receive coil may be affixed to a first surface of a flexible ferrite sheet. The flexibility of the ferrite sheet and the windings forming the receive coil allow the combination of the ferrite sheet and the affixed receive coil to be affixed, at a second surface of the ferrite sheet opposite the first surface, to a curvature of an inner surface of the housing of a portion of the IMD. This arrangement allows the receive coil to occupy a desired volume in the IMD while allowing for a high level of inductive coupling efficiency to be achieved between the receive coil and externally generated magnetic field(s) that are imposed onto the receive coil, which may be enhanced by the presence of the interposing ferrite sheet, for the purpose of providing inductive recharging of a power source located with the IMD, such as a battery or a supercapacitor.

When there is a need to recharge a power source of an IMD that includes a receive coil configuration as described in this disclosure, the device including the receive coil configuration may be placed within a magnetic field (or within a resultant magnetic field formed by a plurality of magnetic fields), which is generated by an externally powered device having one or more transmit coils (also referred to as primary coils) so that the magnetic field (or the resultant magnetic field) is imposed onto the receive coil of the IMD. The magnetic field(s) imposed on the device may be arranged to induce electrical current(s) into one or more of the windings of the receive coil. The induced electrical current or currents may be used to recharge the power source of the IMD and/or to provide the electrical power used to directly operate the device.

Examples described in this disclosure are directed to an IMD comprising a rechargeable battery comprising a battery housing; a non-metallic substrate attached to the battery housing, wherein the non-metallic substrate and the battery housing form an outer housing of the implantable medical device; control circuitry formed on the non-metallic substrate and located within the outer housing of the implantable medical device, wherein the control circuitry is configured to control functioning of the implantable medical device; a receive coil within the outer housing of the implantable medical device, the receive coil configured to receive energy from outside of the outer housing of the implantable medical device; and recharge circuitry within the outer housing of the implantable medical device and coupled to the receive coil, the recharge circuitry configured to receive the energy from the receive coil, and recharge the rechargeable battery using the received energy.

Examples described in this disclosure are directed to a system for recharging a power source located in an IMD implanted in a patient, the system comprising an electrical power source; at least one recharging coil coupled to the electrical power source and configured to generate a magnetic field having a magnetic field direction when electrically energized by the electrical power source; and an implantable medical device comprising a rechargeable battery comprising a battery housing; a non-metallic substrate attached to the battery housing, wherein the non-metallic substrate and the battery housing form an outer housing of the implantable medical device; control circuitry formed on the non-metallic substrate and located within the outer housing of the implantable medical device, wherein the control circuitry is configured to control functioning of the implantable medical device; a receive coil within the outer housing of the implantable medical device, the receive coil configured to receive energy from the at least one recharging coil outside of the outer housing of the implantable medical device; and recharge circuitry within the outer housing of the implantable medical device and coupled to the receive coil, the recharge circuitry configured to receive the energy from the receive coil, and recharge the rechargeable battery using the received energy.

Examples described in this disclosure are directed to a method for recharging a power source located in an IMD implanted in a patient, the method comprising receiving, at a receive coil configuration of the implantable medical device, a magnetic field generated by at least one recharging coil located externally to the patient, wherein the magnetic field induces one or more electrical currents in at least one receive coil forming the receive coil configuration, wherein the implantable medical device comprises the rechargeable battery comprising a battery housing; a non-metallic substrate attached to the battery housing, wherein the non-metallic substrate and the battery housing form an outer housing of the implantable cardiac monitor device; control circuitry formed on the non-metallic substrate and located within the outer housing of the implantable medical device, wherein the control circuitry is configured to control functioning of the implantable cardiac monitor device; a receive coil within the outer housing of the implantable cardiac monitor device, the receive coil configured to receive energy from the at least one recharging coil outside of the outer housing of the implantable medical device; and recharge circuitry within the outer housing of the implantable cardiac monitor device and coupled to the receive coil, the recharge circuitry configured to receive the energy from the receive coil, and recharge the rechargeable battery using the received energy; generating, using the receive coil configuration, one or more electrical currents induced into the at least one receive coil when an externally generated magnetic field is received at the at least one receive coil; summing, by recharging circuitry, the one or more electrical currents to form a recharging current; and applying, by the recharging circuitry, the recharging current to the rechargeable battery of the implantable medical device to recharge the energy level stored in the rechargeable battery.

Examples described in this disclosure are directed to a system comprising an implantable cardiac monitor device comprising a rechargeable battery comprising a battery housing; a non-metallic substrate attached to the battery housing, wherein the non-metallic substrate and the battery housing form an outer housing of the implantable cardiac monitor device; control circuitry formed on the non-metallic substrate and located within the outer housing of the implantable medical device, wherein the control circuitry is configured to control functioning of the implantable cardiac monitor device; a receive coil within the outer housing of the implantable cardiac monitor device, the receive coil configured to receive energy from the at least one recharging coil outside of the outer housing of the implantable medical device; and recharge circuitry within the outer housing of the implantable cardiac monitor device and coupled to the receive coil, the recharge circuitry configured to receive the energy from the receive coil, and recharge the rechargeable battery using the received energy; wherein the at least one implantable pacemaker device is configured to communicate telemetry data to the implantable cardiac monitor device; and the implantable cardiac monitor device is configured to communicate the telemetry data to a mobile device via a short-range wireless communication protocol.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF THE FIGURES

The details of one or more examples of this disclosure are set forth in the accompanying drawings and the description below. Other features, objects, and advantages of this disclosure will be apparent from the description, drawings, and claims.

Figure 1:
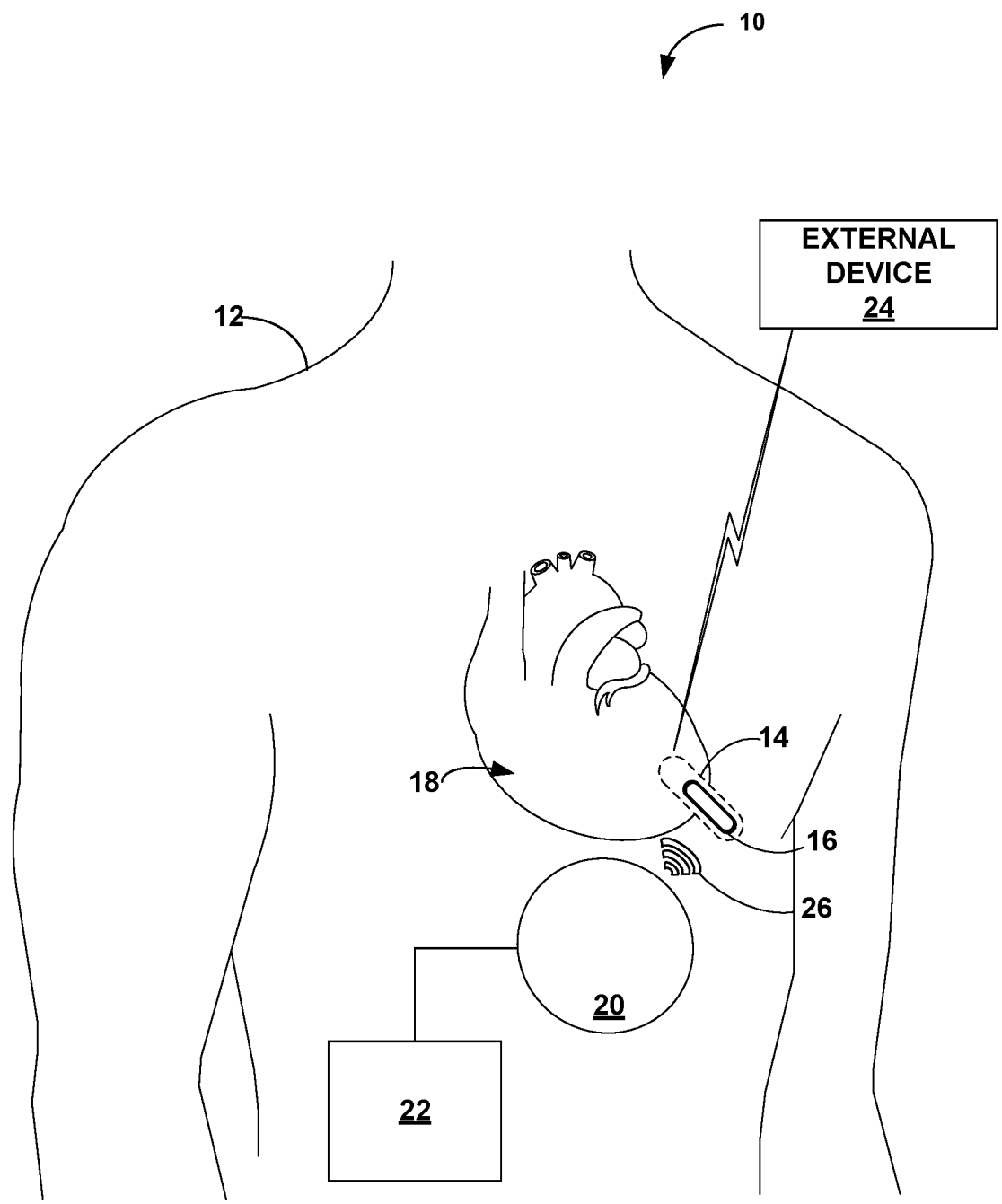
FIG. 1 is a conceptual drawing illustrating an example medical device system in conjunction with a patient according to various examples described in this disclosure.

In the figures, use of a same reference number or a same reference number with a letter extension may be used to indicate a same or corresponding device or element when used in a same drawing or in different drawings. In addition, unless otherwise indicated, devices and/or other objects such as a patient, an implantable medical device, or an electrical device such as an electrical coil, are not necessarily illustrated to scale relative to each other and/or relative to an actual example of the item being illustrated. In particular, various drawings provided with this disclosure illustrate a "patient" represented by a human-shaped outline, and are not to be considered drawn to scale relative to an actual human patient or with respect to other objects illustrated in the same figure unless otherwise specifically indicated in the figure for example by dimensional indicators, or for example as otherwise described in the text of the disclosure.

DETAILED DESCRIPTION

A variety of types of medical devices sense cardiac electrograms (EGMs) and/or other physiological signals or parameters of a patient. Some medical devices that sense cardiac EGMs and/or other patient signals or parameters are non-invasive, e.g., using a plurality of electrodes placed in contact with external portions of the patient, such as at various locations on the skin of the patient to sense cardiac EGMs. The electrodes used to monitor the cardiac EGM in these non-invasive processes may be attached to the patient using an adhesive, strap, belt, or vest, as examples, and electrically coupled to a monitoring device, such as an electrocardiograph, Holter monitor, or other electronic device. The electrodes are configured to sense electrical signals associated with the electrical activity of the heart or other cardiac tissue of the patient, and to provide these sensed electrical signals to the electronic device for further processing and/or display of the electrical signals. The non-invasive devices and methods may be utilized on a temporary basis, for example to monitor a patient during a clinical visit, such as during a doctor's appointment, or for example for a predetermined period of time, for example for one day (twenty-four hours), or for a period of several days.

External devices that may be used to non-invasively sense and monitor cardiac EGMs include wearable devices with electrodes configured to contact the skin of the patient, such as patches, watches, or necklaces. One example of a wearable physiological monitor configured to sense a cardiac EGM is the SEEQ™ Mobile Cardiac Telemetry System, available from Medtronic plc, of Dublin, Ireland. Such external devices may facilitate relatively longer-term monitoring of patients during normal daily activities, and may periodically transmit collected data to a network service, such as the Medtronic Carelink™ Network.

Some IMDs also sense and monitor cardiac EGMs. The electrodes used by IMDs to sense cardiac EGMs are typically integrated with a housing of the IMD and/or coupled to the IMD via one or more elongated leads. Example IMDs that monitor cardiac EGMs include pacemakers and implantable cardioverter-defibrillators, which may be coupled to intravascular or extravascular leads, as well as pacemakers with housings configured for implantation within the heart, which may be leadless. An example of pacemaker configured for intracardiac implantation is the Micra™ Transcatheter Pacing System, available from Medtronic plc. Some IMDs that do not provide therapy, e.g., implantable patient monitors, sense cardiac EGMs. One example of such an IMD is the Reveal LINQ™ Insertable Cardiac Monitor (ICM), available from Medtronic plc, which may be inserted subcutaneously. Such IMDs may facilitate relatively longer-term monitoring of patients during normal daily activities, and may periodically transmit collected data to a network service, such as the Medtronic Carelink™ Network.

Traditional cardiac monitors, pacemakers, neurostimulators and implantable loop recorders may use primary batteries with finite energy as an internal power source for electrically powering operation of the device once the device has been implanted in a patient. In various examples of IMDs, a primary (non-rechargeable) battery has a finite energy reservoir which limits its mission life based on its size and energy density (for a given energy usage rate). This limits the useful duration of the implanted device. Once a primary battery is exhausted, replacement of the device may be required, and although replacement of the device may be minimally invasive, it may still present procedural risks for the patient.

In addition, limits on the available battery energy may result in limits to therapy and/or monitoring options for a device and/or the patient. Further, issues related to the IMD may result in a need for a more energy-consuming device configuration, which can further shorten the mission life of the IMD. For example, detectable cardiac events may occur more frequently in certain patients, resulting in the IMD needing to more frequently process, store, and communicate data, causing excessive battery drain and reduced longevity of the IMD.

A rechargeable battery conceptually offers a semi-infinite reservoir of energy in which the size of the battery and charged energy density determines the recharge frequency rather than the mission life (under the assumption of negligible battery capacity fade). A result of a semi-infinite energy source is the opportunity to provide additional features and functions that may otherwise be limited or unavailable given a finite energy source constraint. Another result of this semi-infinite energy source is the potential reduction or elimination of a need to perform a surgically invasive device replacement procedure required due to exhausting the capacity of the primary (i.e., non-rechargeable) battery. Receive coil configurations as described herein may be incorporated within a relatively compact IMD, such as the LINQ™ ICM.

The ability to recharge the power source of an IMD, for example within a one-hour recharging period of time on a monthly or yearly cycle, without the need to explant the device to do so, allows at least the benefits described above, including use of a smaller power source to help miniaturize the IMD itself, and to allow more power, and thus greater functionality for the implanted medical device by providing an overall longer mission lifespan for the device using a smaller-sized power source. Examples of the receive coil configurations as described in this disclosure have been shown to safely deliver over 80 milliwatts of power to the rechargeable battery of the implanted device.

Throughout the disclosure, a reference to a "receive coil" refers to a coil winding formed from an electrical conductor that may or may not be coupled with one or more additional coil windings to form a receive coil for an implantable medical device. The use of the term "receive antenna" may be used in place of or interchangeably with the term "receive coil" in any context referring to a coil winding that is coupled to recharging circuitry of an implantable medical device and that may be configured to have current induced into the coil winding for the purpose of providing electrical energy to recharging a rechargeable power source of the implantable medical device and/or to provide electrical power to operate the electrical circuitry of the implanted medical device for the purpose of operating the device.

Throughout the disclosure reference is made to a "magnetic field" or to "magnetic fields" in the context of a magnetic field or magnetic fields that is/are generated externally to an IMD, and imposed onto the IMD for the purpose of inducing a current into one or more coil windings of a receive coil of the implantable medical device. In general, such a magnetic field or magnetic fields have a parameter (e.g., amplitude or phase) that varies in time, or that varies in time with respect to the magnetic field direction of the magnetic field, resulting in a time rate of change of the net magnetic flux intensity imposed onto the coil windings of the receive coil, and a corresponding change in the electromotive force (emf) configured to generate a current or currents in the one or more coil windings.

FIG. 1 is a conceptual drawing illustrating an example medical system 10 in conjunction with a patient 12 according to various examples described in this disclosure. The systems, devices, and methods described in this disclosure may include examples configurations of a receive coil 16 located within an IMD 14, for charging of IMD 14, as illustrated and described with respect to FIG. 1. For purposes of this description, knowledge of cardiovascular anatomy and functionality is presumed, and details are omitted except to the extent necessary or desirable to explain the context of the techniques of this disclosure. System 10 includes rechargeable IMD 14 having receive coil 16, implanted at or near the site of a heart 18 of a patient 12; a transmit coil 20 coupled to external recharging device 22; and an external computing device 24. The systems, devices, and methods described herein may provide efficient inductive coupling of an external recharging device 22 to the electrical circuitry that is internal to IMD 14.

The example techniques may be used with IMD 14, which may be in wireless communication with at least one of external device 24 and other devices not pictured in FIG. 1. In some examples, IMD 14 is implanted outside of a thoracic cavity of patient 12 (e.g., subcutaneously in the pectoral location illustrated in FIG. 1). IMD 14 may be positioned near the sternum near or just below the level of the heart of patient 12, e.g., at least partially within the cardiac silhouette. IMD 14 includes a plurality of electrodes 48 (FIG. 5), and is configured to sense a cardiac electrogram (EGM) via the plurality of electrodes. In some examples, IMD 14 takes the form of the LINQ™ ICM, or another ICM similar to, e.g., a version or modification of, the LINQ™ ICM. Although described primarily in the context of examples in which IMD 14 is an ICM, in various examples, IMD 14 may represent a cardiac monitor, a defibrillator, a cardiac resynchronization pacer/defibrillator, a pacemaker, an implantable pressure sensor, a neurostimulator, or any other implantable or external medical device.

External device 24 may be a computing device with a display viewable by the user and an interface for providing input to external device 24 (i.e., a user input mechanism). In some examples, external device 24 may be a notebook computer, tablet computer, workstation, one or more servers, cellular phone, personal digital assistant, or another computing device that may run an application that enables the computing device to interact with IMD 14. External device 24 is configured to communicate with IMD 14 and, optionally, another computing device (not illustrated in FIG. 1), via wireless communication. External device 24, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies).

External device 24 may be used to configure operational parameters for IMD 14. External device 24 may be used to retrieve data from IMD 14. The retrieved data may include values of physiological parameters measured by IMD 14, indications of episodes of arrhythmia or other maladies detected by IMD 14, and physiological signals recorded by IMD 14. For example, external device 24 may retrieve cardiac EGM segments recorded by IMD 14, e.g., due to IMD 14 determining that an episode of arrhythmia or another malady occurred during the segment, or in response to a request to record the segment from patient 12 or another user. In some examples, one or more remote computing devices may interact with IMD 14 in a manner similar to external device 24, e.g., to program IMD 14 and/or retrieve data from IMD 14, via a network.

In various examples, IMD 14 may include one or more additional sensor circuits configured to sense a particular physiological or neurological parameter associated with patient 12, or may comprise a plurality of sensor circuits, which may be located at various and/or different positions relative to patient 12 and/or relative to each other, and may be configured to sense one or more physiological parameters associated with patient 12.

For example, IMD 14 may include a sensor operable to sense a body temperature of patient 12 in a location of the IMD 14, or at the location of the patient where a temperature sensor coupled by a lead to IMD 14 is located. In another example, IMD 14 may include a sensor configured to sense motion, such as steps taken by patient 12 and/or a position or a change of posture of patient 12. In various examples, IMD 14 may include a sensor that is configured to detect breaths taken by patient 12. In various examples, IMD 14 may include a sensor configured to detect heartbeats of patient 12. In various examples, IMD 14 may include a sensor that is configured to measure systemic blood pressure of patient 12.

In some examples, one or more of the sensors comprising IMD 14 may be implanted within patient 12, that is, implanted below at least the skin level of the patient. In some examples, one or more of the sensors of IMD 14 may be located externally to patient 12, for example as part of a cuff or as a wearable device, such as a device imbedded in clothing that is worn by patient 12. In various examples, IMD 14 may be configured to sense one or more physiological parameters associated with patient 12, and to transmit data corresponding to the sensed physiological parameter or parameters to external device 24, as represented by the lightning bolt coupling IMD 14 to external device 24.

Transmission of data from IMD 14 to external device 24 in various examples may be performed via wireless transmission, using for example any of the formats for wireless communication described above. In various examples, IMD 14 may communicate wirelessly to an external device (e.g., an instrument or instruments) other than or in addition to external device 24, such as a transceiver or an access point that provides a wireless communication link between IMD 14 and a network. In various examples, a transceiver is communication circuitry included within recharging circuitry 22, wherein communication circuitry of external recharging device 22 is configured to communicate with IMD 14 during the recharging process, as further described below. Examples of communication techniques used by any of the devices described above with respect to FIG. 1 may include radiofrequency (RF) telemetry, which may be an RF link established via Bluetooth®, Wi-Fi, or medical implant communication service (MICS).

In some examples, system 10 may include more or fewer components than depicted in FIG. 1. For example, in some examples, system 10 may include multiple additional IMDs, such as implantable pacemaker devices or other IMDs, implanted within patient 12. In these examples, rechargeable IMD 14 may function as a hub device for the other IMDs. For example, the additional IMDs may be configured to communicate with the rechargeable IMD 14, which would then communicate to the external device 24, such as a user's smartphone, via a low-energy telemetry protocol. Rechargeable IMD 14 may provide a theoretically infinite energy capacity, in that IMD 14 may not need to be replaced or otherwise removed. Accordingly, IMD 14 may provide the ability to more-frequently telemeter information, as well as more-active titration of therapies.

For the remainder of the disclosure, a general reference to a medical device system may refer collectively to include any examples of medical device system 10, a general reference to IMD 14 may refer collectively to include any examples of IMD 14, a general reference to sensor circuits may refer collectively to include any examples of sensor circuits of IMD 14, and a general reference to an external device may refer collectively to any examples of external device 24.

Figure 2:
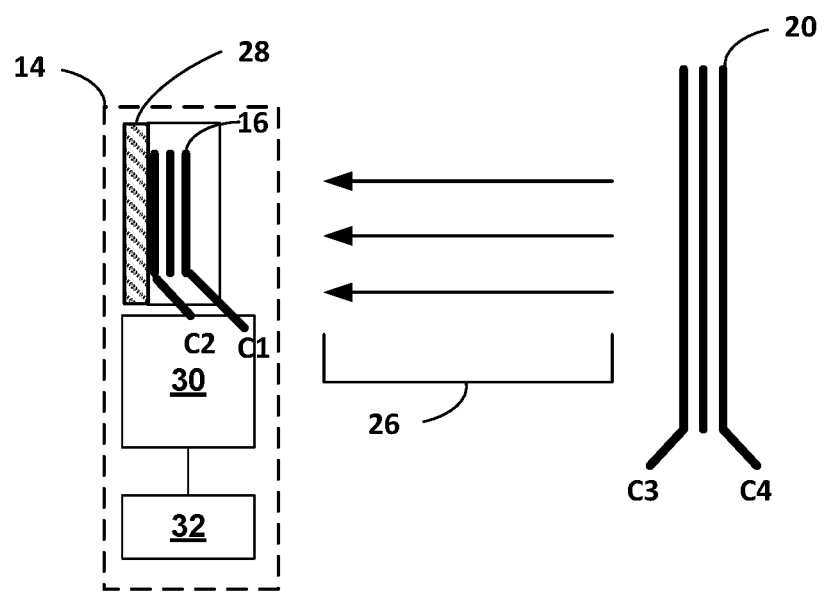
FIG. 2 is a conceptual drawing illustrating magnetic a field imposed onto a receive coil affixed to a ferrite sheet, according to various examples described in this disclosure.

FIG. 2 is a conceptual drawing illustrating a magnetic field 26 imposed onto a receive coil 16 of IMD. As shown in FIG. 2, receive coil 16 is affixed to a surface of a ferrite sheet 28. Receive coil 16 includes an electrical conductor formed as the windings of a receive coil according to any of the receive coils described throughout this disclosure, including a flat spiral-wound coil or a tubular coil winding. Receive coil 16 includes a pair of leads C1, C2 that may be coupled to recharging circuitry 30 of IMD 14, which may in turn be coupled to rechargeable battery 32 of IMD 14. Receive coil 16 may be a single receive coil, or one of a plurality of receive coils of an IMD according to the various examples described throughout this disclosure.

As shown in FIG. 2, receive coil 16 is affixed to a surface of the ferrite sheet 28. Ferrite sheet 28 may be configured to block extraneous electromagnetic interference (EMI) and/or otherwise boost the efficiency of the power transfer from external recharging coil 20 to receive coil 16. In some examples, ferrite sheet 28 may have a surface area having a perimeter (e.g., a rectangular or square area defined by a height and width dimension) over which the windings of receive coil 16 extend orthogonally to the thickness of ferrite sheet 28. In other words, the height and width dimensions of the windings of receive coil 16 extend adjacent to a surface of ferrite sheet 28 such that all or portions of the windings are in direct contact with, or adjacent to, some portion of a surface of ferrite sheet 28.

As illustrated in FIG. 2, receive coil 16 and ferrite sheet 28, along with recharging circuitry 30 and rechargeable battery 32, may be incorporated within an implantable medical device 14, illustratively represented by a dashed box. A transmit coil 20 (also referred to as "external recharging coil 20") is positioned at some location proximate to IMD 14, e.g., to the right of receive coil 16 in FIG. 2. When positioned as shown in FIG. 2, receive coil 16 is positioned between the first external recharging coil 20 and the ferrite sheet 28.

External recharging coil 20 includes a pair of leads C3, C4 configured to be coupled to external recharging circuitry (not shown in FIG. 2, but for example included within external recharging device 22 of FIG. 1). The external recharging circuitry of external recharging device 22 is configured to electrically energize the external recharging coil 20 and in turn generate a magnetic field, illustratively represented by the arrows indicated by bracket 26. The magnetic field generated by external recharging coil 20 may be imposed onto the implantable medical device including receive coil 16 in the direction indicated by the arrows (bracket 26) extending from external recharging coil 20 toward receive coil 16. The magnetic field generated by external recharging coil 20 may induce a current into the windings of receive coil 16, which may then be coupled to recharging circuitry of IMD 14 coupled to receive coil 16.

In various examples of receive coil configurations described below, the receive coil may be bent or shaped into a curved configuration that extends around (e.g., conforms to) a portion of the inner surface of a housing of IMD 14 where the receive coil is installed. Ferrite sheet 28 may be affixed to receive coil 16 and oriented and/or shaped to configuration of the location within IMD 14 in which they are located and, in some cases, so that a wide variety of different orientations of the direction of the magnetic fields 26 that may be imposed onto the IMD 14 that may benefit from the increased level of inductive coupling efficiency associated with the use of the ferrite sheets 28 as described above. Various arrangements of ferrite sheet(s) 28, receive coil(s) 16, and battery 32 that may be provided within an IMD and configured to benefit from the "preferred orientation" of the receive coil/ferrite assemblies relative to one or more magnetic fields imposed onto the implantable medical device are illustrated and described in further detail below. Additionally, although a number of examples described herein include a ferrite sheet, other example receive coil configurations do not include a ferrite sheet.

Figure 3:
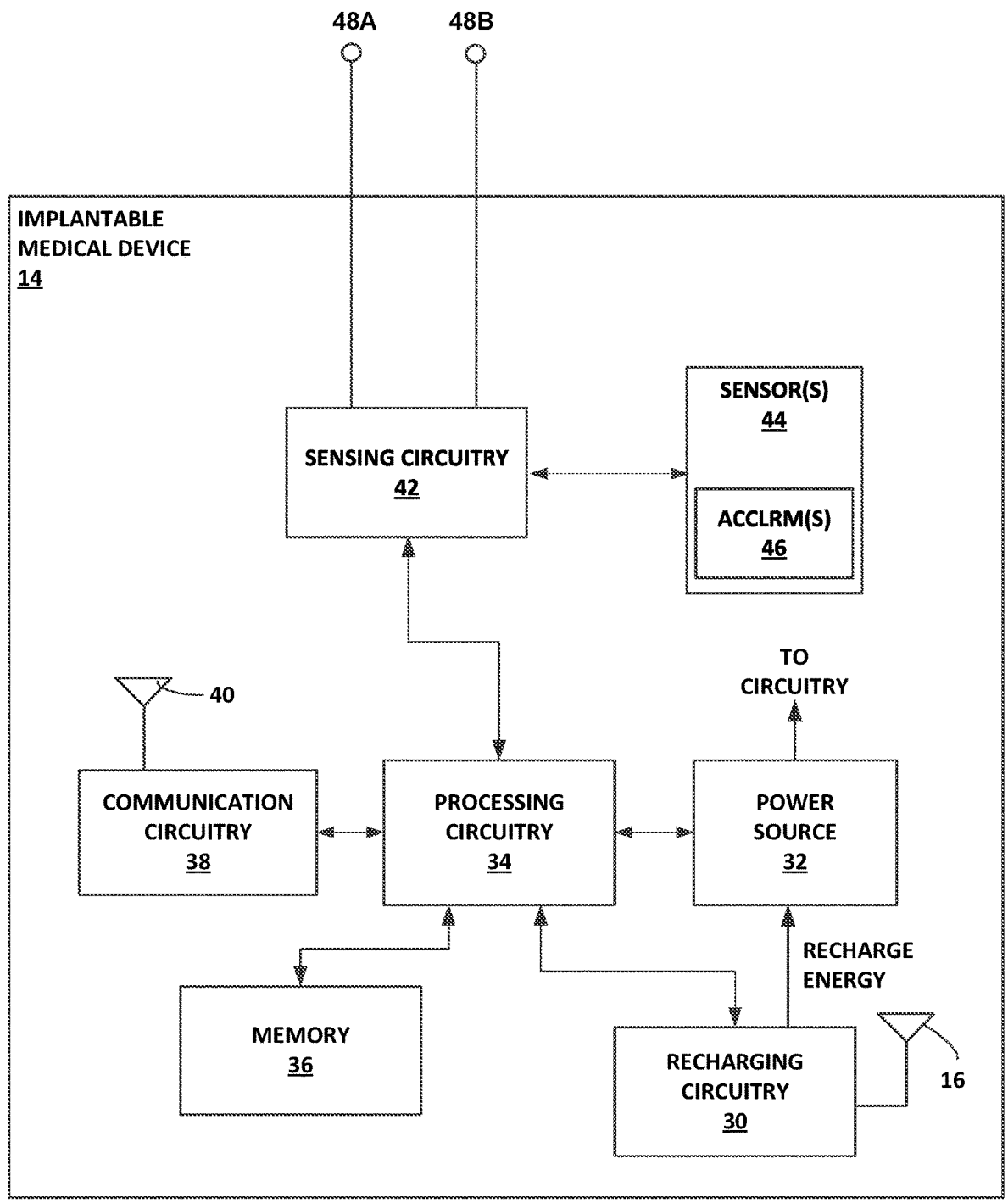
FIG. 3 is a functional block diagram illustrating an example configuration of the implantable medical device (IMD) of the medical system of FIG. 1.

FIG. 3 is a functional block diagram illustrating an example configuration of IMD 14 of medical system 10 of FIG. 1. In the illustrated example, IMD 14 includes receive coil 16, recharging circuitry 30, rechargeable power source 32, processing circuitry 34, memory 36, communication circuitry 38, communication antenna 40, sensing circuitry 42, sensor(s) 44, accelerometer(s) 46, and electrodes 48A and 48B (collectively, "electrodes 48"). Although the illustrated example includes two electrodes 48, IMDs including or coupled to more than two electrodes 48 may implement the techniques of this disclosure in some examples.

Processing circuitry 34 may include fixed function circuitry and/or programmable processing circuitry. Processing circuitry 34 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 34 may include multiple components, such as any combination of one or more microprocessors, one or more controllers, one or more DSPs, one or more ASICs, or one or more FPGAs, as well as other discrete or integrated logic circuitry. The functions attributed to processing circuitry 34 herein may be embodied as software, firmware, hardware or any combination thereof.

Sensing circuitry 42 is coupled to electrodes 48. Sensing circuitry 42 may sense signals from electrodes 48, e.g., to produce a cardiac EGM, in order to facilitate monitoring the electrical activity of the heart. Sensing of a cardiac EGM may be done to determine heart rates or heart rate variability, or to detect arrhythmias (e.g., tachyarrhythmias or bradycardia). Sensing circuitry 42 may additionally monitor impedance or other electrical phenomena via electrodes 48. Sensing circuitry 42 also may monitor signals from sensors 44, which may include one or more accelerometers 46, pressure sensors, and/or optical sensors, as examples. In some examples, sensing circuitry 42 may include one or more filters and amplifiers for filtering and amplifying signals received from electrodes 48 and/or sensors 44. In some examples, sensing circuitry 42 may sense or detect physiological parameters, such as heart rate, blood pressure, respiration, and other physiological parameters associated with a patient.

Sensing circuitry 42 and/or processing circuitry 34 may be configured to detect cardiac depolarizations (e.g., P-waves of atrial depolarizations or R-waves of ventricular depolarizations) when the cardiac EGM amplitude crosses a sensing threshold. For cardiac depolarization detection, sensing circuitry 42 may include a rectifier, filter, amplifier, comparator, and/or analog-to-digital converter, in some examples. In some examples, sensing circuitry 42 may output an indication to processing circuitry 34 in response to sensing of a cardiac depolarization. In this manner, processing circuitry 34 may receive detected cardiac depolarization indicators corresponding to the occurrence of detected R-waves and P-waves in the respective chambers of heart. Processing circuitry 34 may use the indications of detected R-waves and P-waves for determining inter-depolarization intervals, heart rate, and detecting arrhythmias, such as tachyarrhythmias and asystole.

Sensing circuitry 42 may also provide one or more digitized cardiac EGM signals to processing circuitry 34 for analysis, e.g., for use in cardiac rhythm discrimination. In some examples, processing circuitry 34 may store the digitized cardiac EGM in memory 36. Processing circuitry 34 of IMD 14, and/or processing circuitry of another device that retrieves data from IMD 14, may analyze the cardiac EGM.

Communication circuitry 38 may include any suitable hardware, firmware, software or any combination thereof for communicating with another device, such as external device 24, another networked computing device, or another IMD or sensor. Under the control of processing circuitry 34, communication circuitry 38 may receive downlink telemetry from, as well as send uplink telemetry to external device 24 or another device with the aid of an internal or external antenna, e.g., antenna 40. In addition, processing circuitry 34 may communicate with a networked computing device via an external device (e.g., external device 24 of FIG. 1) and a computer network, such as the Medtronic CareLink® Network. Antenna 40 and communication circuitry 38 may be configured to transmit and/or receive signals via inductive coupling, electromagnetic coupling, Near Field Communication (NFC), Radio Frequency (RF) communication, Bluetooth, Wi-Fi, or other proprietary or non-proprietary wireless communication schemes. Communication antenna 40 may telemeter data at a high frequency, such as around 2.4 gigahertz (GHz).

In some examples, memory 36 includes computer-readable instructions that, when executed by processing circuitry 34, cause IMD 14 and processing circuitry 34 to perform various functions attributed to IMD 14 and processing circuitry 34 herein. Memory 36 may include any volatile, non-volatile, magnetic, optical, or electrical media, such as a random-access memory (RAM), read-only memory (ROM), non-volatile RAM (NVRAM), electrically erasable programmable ROM (EEPROM), flash memory, or any other digital media. Memory 36 may store, as examples, programmed values for one or more operational parameters of IMD 14 and/or data collected by IMD 14, e.g., posture, heart rate, activity level, respiration rate, and other parameters, as well as digitized versions of physiological signals sensed by IMD 14, for transmission to another device using communication circuitry 38.

IMD 14 includes a rechargeable power source 32 that may be coupled to the electronic circuitry provided in IMD 14, and is configured to provide electrical power to these circuits. Power source 32 may be inductively rechargeable by imposing one or more magnetic fields onto IMD 14, wherein energy from these imposed field(s) may induce an electrical energy into receive coil 16 and, thereby, to recharging circuitry 30.

As shown in FIG. 3, device recharging circuitry 30 is coupled to power source 32, and may receive electrical energy induced in receive coil 16 by one or more electromagnetic fields imposed on the coil, and to regulate the energy to provide a level of energy that is provided to power source 32 for the purpose of recharging power source 32 and/or powering the other circuitry included as part of IMD 14. Device recharging circuitry 30 may perform various energy conditioning functions to the energy inductively generated in receive coil 16, for example by providing rectification, voltage level regulation, current level regulation, and/or other signal processing functions in order to generate the "recharging energy" provided to power source 32.

In the illustrated example, IMD 14 includes processing circuitry 34 and an associated memory 36, sensing circuitry 42, one or more sensors 44, and the communication circuitry 38 coupled to antenna 40 as described above. However, IMD 14 need not include all of these components, or may include additional components.

Processing circuitry 34 may be configured to provide information including a state of charge, and/or temperature information related to a battery, e.g., a battery located in IMD 14, determining a level of inductive coupling, e.g., energy level being generated in a receive coil located in IMD 14 as a result of an electromagnetic field or fields being imposed on IMD 14, and generate information related to this inductively received energy for transmission by the communication antenna or separate antenna and associated power conditioning circuitry of IMD 14.

In various examples, processing circuitry 34 is coupled to device recharging circuitry 30, and receives information, such as a level of current, that is being induced in coil 16 as a result of electrical energy received by the antenna via magnetic energy imposed on IMD 14 for the purpose of recharging power source 32. Processing circuitry 34 may provide this and other information, for example charge rate and temperature information associated with the power source 32, in the form of an output signal to communication circuitry 38 for transmission from IMD 14 to one or more external devices, such as external recharging device 22 (FIG. 1). This transmitted information may be used by the external device(s) to control one or more aspects of the recharging process.

For example, positioning of and/or a level of power being applied to a recharging coil or a pair of coils located externally to IMD 14 and generating the magnetic field or fields being imposed on IMD 14 may be controlled using this information transmitted from IMD 14. The setting of electrical parameters used to energize the coil of the pair of coils generating the magnetic field or fields imposed onto IMD 14 for the purpose of recharging the power source 32 may be controlled using this information transmitted from IMD 14. In addition, other information such as temperature and field intensity information transmitted from IMD 14, may be used to control the recharging process, for example by regulating the field strength being generated by the external coil(s), or for example to shut off the external coil(s) to stop the recharging process.

Figure 4:
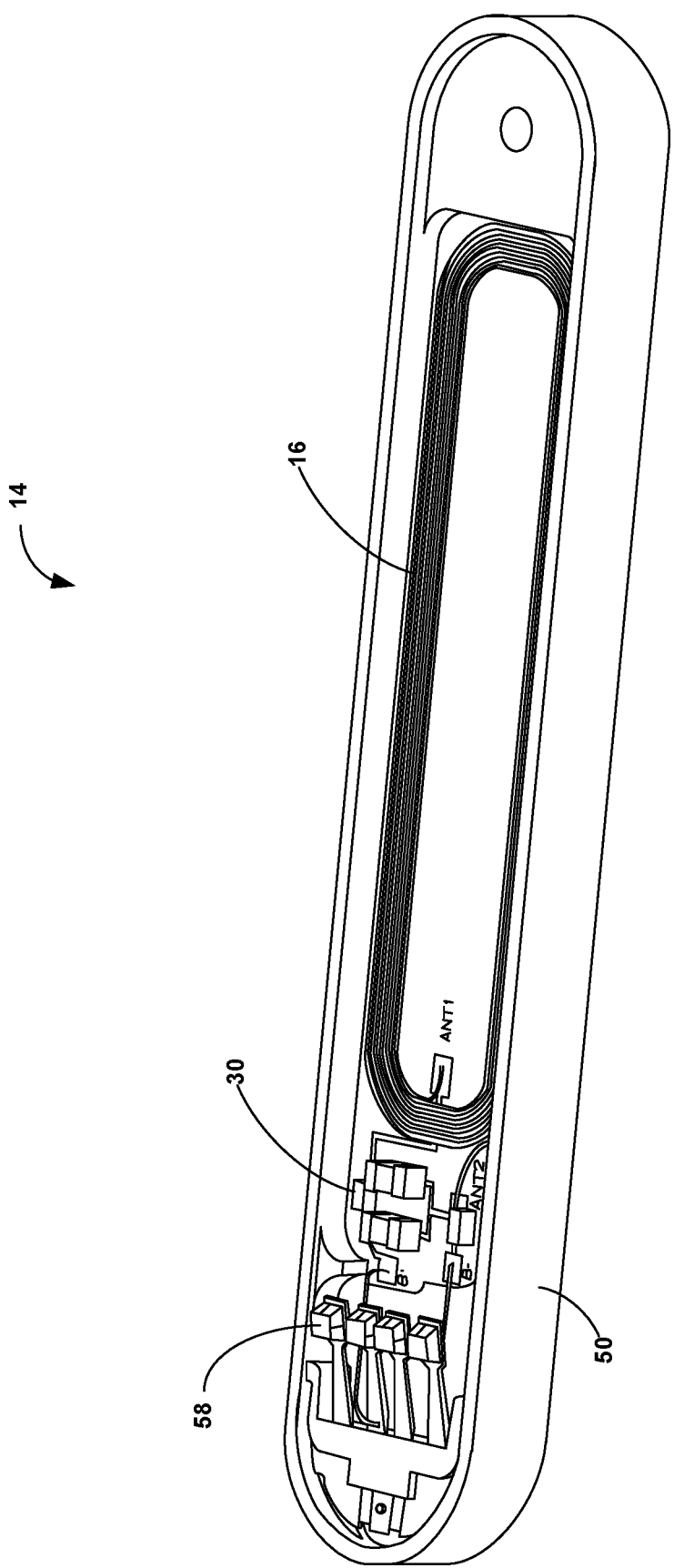
FIG. 4 is an oblique view of an example rechargeable implantable medical device having a receive coil, according to various examples of this disclosure.
Figure 5:
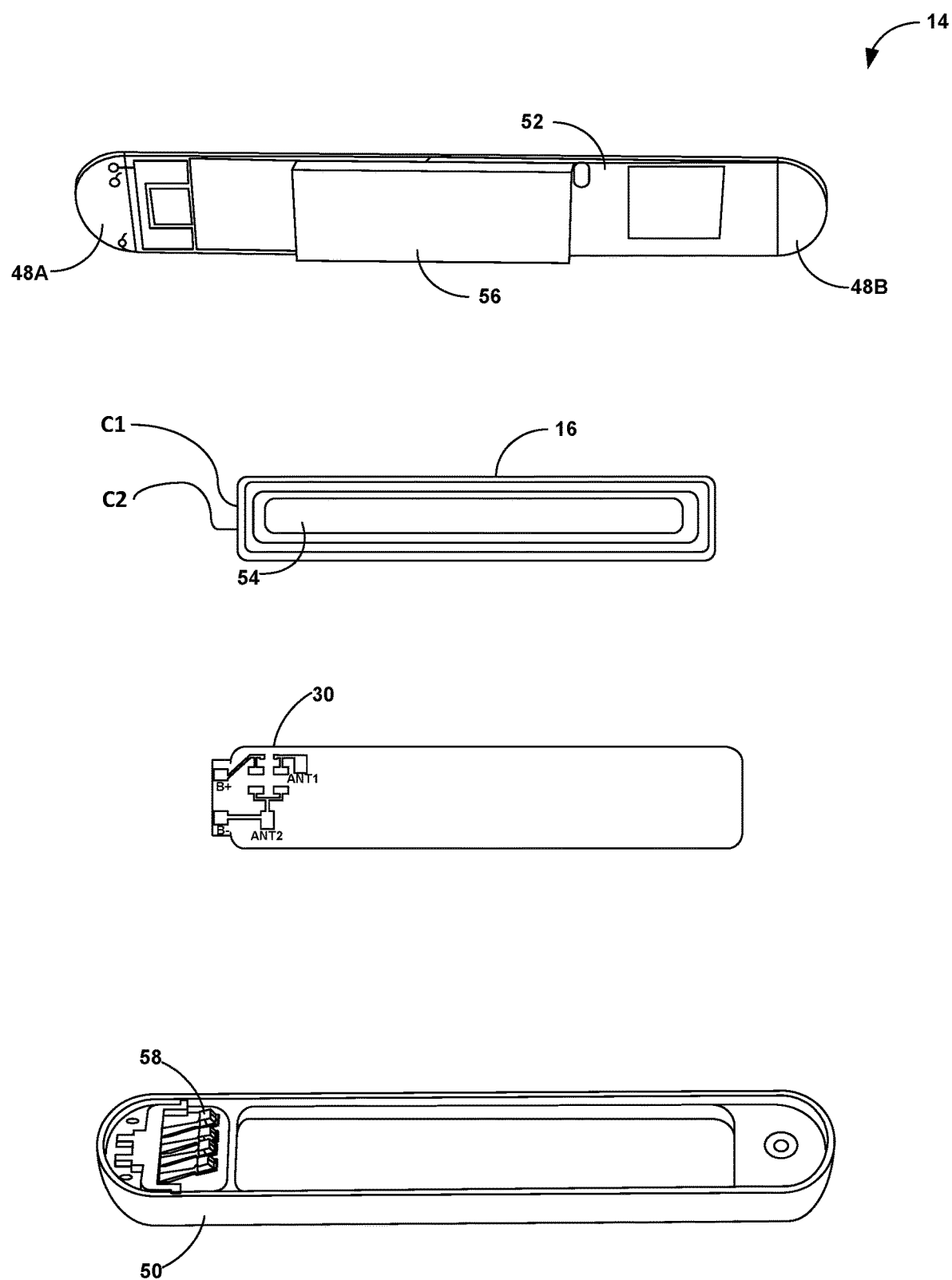
FIG. 5 is an exploded view of the example rechargeable implantable medical device of FIG. 4.

FIG. 4 is an oblique view of an example configuration of rechargeable IMD 14 having a receive coil 16, according to various examples of this disclosure. IMD 14 may be an example of an insertable cardiac monitor (ICM), configured to sense and monitor cardiac EGMs via one or more electrodes 48 (FIGS. 3 and 5). For example, IMD 14 may include a Reveal LINQ™ Insertable Cardiac Monitor, available from Medtronic plc, which may be inserted subcutaneously. Such IMDs may facilitate relatively longer-term monitoring of patients during normal daily activities, and may periodically transmit collected data to a network service, such as the Medtronic Carelink™ Network. In the illustrated example, receive coil 16 has a substantially planar configuration. In other examples detailed further below, an IMD may include a receive coil having a tubular configuration, in which individual coil loops are stacked on top of one another. In either case, receive coil 16 is configured to receive electromagnetic energy from a separate external recharging coil 20 (FIG. 1), in order to recharge a rechargeable battery or other power source 32 (FIG. 2) located within a battery housing 50 of the device.

In the illustrated example, recharge circuitry 30, which is electrically connected to the two leads of coil 16, is located adjacent to an outside of the coil, and substantially coplanar with receive coil 16. Power source 32 is contained within battery housing 50 beneath receive coil 16, and is not shown in FIG. 4. One or more sidewalls of battery housing 50 define a recess within which receive coil 16 and recharge circuitry 30 are located. Although not shown in FIG. 4, IMD 14 may include a cover configured to be attached (e.g., sealed) to battery housing 50 and thereby form an outer housing (e.g., an enclosure) of IMD 14, within which receive coil 16 and recharge circuitry 30 are located. As will be described in greater detail below, circuitry may be formed on the cover and connected to power source 32 by electrical contacts 58.

FIG. 5 is an exploded view of the example rechargeable IMD 14 of FIG. 4. IMD 14 includes at least a receive coil 16, recharge circuitry 30, battery housing 50, and cover 52. Recharge circuitry 30 is coupled to a rechargeable battery or other power source, and may receive electrical energy induced in receive coil 16 by one or more electromagnetic fields imposed on the antenna, and to regulate the energy to provide a level of energy that is provided to the power source for the purpose of recharging the power source and/or powering the other circuitry included as part of IMD 14. Recharge circuitry 30 may perform various energy conditioning functions to the energy inductively generated in receive coil 16, for example by providing rectification, voltage level regulation, current level regulation, and/or other signal processing functions in order to generate the "recharging energy" provided to the power source.

IMD 14 includes a tub-shaped hull or battery housing 50. In some examples, battery housing 50 is formed of a material such as titanium or a titanium alloy, and may be sealingly joined to cover 52. When joined, cover 52 and battery housing 50 may form a sealed housing or enclosure for circuitry of IMD 14, including receive coil 16 and recharge circuitry 30.

For more low frequency applications (e.g., magnetic fields having a frequency of 200 kHz or less), battery housing 50 may be formed of material that includes a titanium alloy that allows magnetic fields having these lower frequencies to pass through the housing and be imposed onto the receive coils 16. In various examples, housing 50 may be formed a biocompatible ceramic material. In some examples, Grade 1 titanium is not a preferred material for housing 50, because Grade 1 titanium may reduce power transfer efficiency as well as convert the drawn power into heat, which may overheat IMD 14 at higher power-transfer levels. Accordingly, a more electrically and thermally resistive material for housing 50, such as titanium Grade 5 or higher, may improve power transfer performance. For example, because Grade 5 titanium may include a higher bulk resistivity than Grade 1 titanium, the use of Grade 5 titanium may reduce power loss attributable to eddy currents.

In some examples, but not all examples, receive coil 16 may be attached to a ferrimagnetic substrate 54. For example, substrate 54 may include a flexible layer of ferrite, which may improve the performance of receive coil 16, particularly when antenna 16 is operating at relatively higher frequencies. For example, when driven at a frequency of between about 400 kHz up to a few MHz, a ferrite backing layer 54 may boost the performance of receive coil 16.

In some examples, cover 52 includes a relatively thin, planar wafer sealingly coupled to battery housing 50. Cover 52 may be formed of a non-metallic or non-conductive substrate material, for example a material having a relatively high value of electrical resistivity, that allows for transmission of the electromagnetic energy being imposed onto IMD 14 for recharging purposes to penetrate and pass through the cover 52, and reach the receive coil 16. Cover 52 may be formed from a "radio transmissive" material that also provides a low relative dielectric constant (i.e., high relative electrical resistivity), and low magnetic permeability. In this manner, cover 52 may provide a relatively more radio transmissive window for receive coil 16 than battery housing 50.

Electrical resistivity may be represented by the Greek letter $\rho$ (rho), and in International System (SI) units is measured in ohmmeter ($\Omega \cdot m$), and which may vary for a given material based on temperature. An example of a material, such as certain metals, that may be considered to be a good electrical conductor and thus have a low value for electrical resistivity, is copper, having a $\rho$ value of approximately $1.68 \times 10^{-8}$ $\Omega$-meter at 20 degrees Celsius (° C.). An example of a material that may be considered to be poor conductors of electricity, e.g, an electrical insulator, and thus having a high value for $\rho$ may include glass, which can have a $\rho$ value in a range of $1 \times 10^{10}$ to $1 \times 10^{14}$ $\Omega$-meter at 20° C. Another example of a material having a high value for $\rho$ is sapphire, which in some examples has a $\rho$ value of in a range of $1 \times 10^{14}$ $\Omega$-centimeter at 23° C. Example of materials having low dielectric constants, high electrical resistivity, and low magnetic permeability that may be used for portions of housing 50 that include a receive coil configuration according to the examples described in this disclosure may include titanium alloy grade 5, 9, 23, 36, which may provide an adequate level of radio transmissivity at lower frequencies, such as up to 200K Hz, or ceramic material that may provide radio transmissivity at these lower frequencies and frequencies above the 200 k Hz frequency range, for example for frequency ranges up to 10 MHz. Metal ceramics made using a metal injection molding process may also be used for a wide range of frequencies similar to the operating frequency ranges for ceramics.

In order to allow higher frequency magnetic fields to reach receive coil 16, at least cover 52 of IMD 14 may be formed of a material, such as sapphire, that has a high value for electrical resistivity, at least at temperatures normally experienced by devices after being implanted within a patient, e.g., temperatures normally not to exceed 39 to 40° C. on the exterior surface of the implanted device even for a brief period of time, that may occur when the device is being recharged. To allow use of higher frequency magnetic fields for the purpose of recharging IMD 14, cover 52 may be made of a radio transparent material having high electrical resistivity (e.g., in a range of $1 \times 10^{11}$ to $1 \times 10^{16}$ Ohms-centimeter) and a low magnetic permeability. A wide range of materials will satisfy these requirements, including examples such as sapphire, a glass material, or polymeric materials are typically employed having a dielectric constant ranging from about 1 to 12. Use of sapphire or a glass material for cover 52 may allow a higher frequency of an induced magnetic field to be transmitted through the cover 52 and be imposed on receive coil 16 relative to other materials that may not provide a same level, or as high a value, for electrical resistivity. For example, by using an cover 52 made from sapphire, magnetic fields having frequencies ranging from about 100 KHz to 10 MHz may be imposed on IMD 14, wherein the sapphire allows the imposed magnetic field or fields having a frequency in this range to pass through the cover 52 and induce a current in an electrical conductor forming the windings of receive coil 16.

As demonstrated in FIG. 11 below, the ability to use higher frequency magnetic fields allows for more energy, and thus a larger current, to be induced into the electrical conductor forming the windings of receive coil 16 at any given time, or over a particular time period during which the higher frequencies are being imposed on IMD 14, as compared to using a lower frequency magnetic field. Cover 52 is not limited to being formed from a visually transparent material. Examples of material used to form cover 52 may include any type of material having a minimum value for electrical resistivity (e.g., a good electrical insulator with low dielectric constant value) and low magnetic permeability, and that meets other manufacturing requirements and complies with any other applicable regulatory requirements, such as biocompatibility requirements, for use in implantable medical devices.

Electrodes 48 are located, e.g., formed on, cover 52 and, in the illustrated example, are positioned on opposite ends of the wafer, as measured along a longitudinal axis of cover 52. In the illustrated example, electrodes 48 have a semi-circular shape, e.g., to conform to the shape of the ends of cover 52. In other examples, IMD 14 may include more electrodes, differently shaped electrodes, and/or electrodes that are not necessarily formed on cover 52. IMD 14 may be configured to sense a cardiac ECG signal and/or other electrical signals via electrodes 48. Electrodes 48 may be formed on an opposite surface of cover 52 than control circuitry 56.

Spring contacts 58 may include one or more elongated, electrically conductive extensions configured to transfer electrical power from battery 32 to control circuitry 56. For example, a first end of each of spring contacts 58 may be rigidly coupled to battery 32, and a second end of each of spring contacts 58 may be configured to physically contact, via an internal spring mechanism, an electrical contact disposed on the same side of cover 52 on which control circuitry 56 is formed.

IMD 14 includes control circuitry 56. Control circuitry 56 includes one or more processors (such as processing circuitry 34 of FIG. 3), microchips, microprocessors, semiconductors, memory units (such as memory 36 of FIG. 3), or other computing components configured to control the operations of IMD 14. As shown in FIG. 5, control circuitry 56 may be formed on the non-metallic substrate of cover 52. Control circuitry 56 may be formed on a surface of cover 52 intended to be inside the enclosure of IMD 14 when cover 52 is mounted on battery housing 50. Sensing circuitry 42, sensors 44, and communication circuitry 38 may be similarly formed on or attached to cover 52.

Figure 6A:
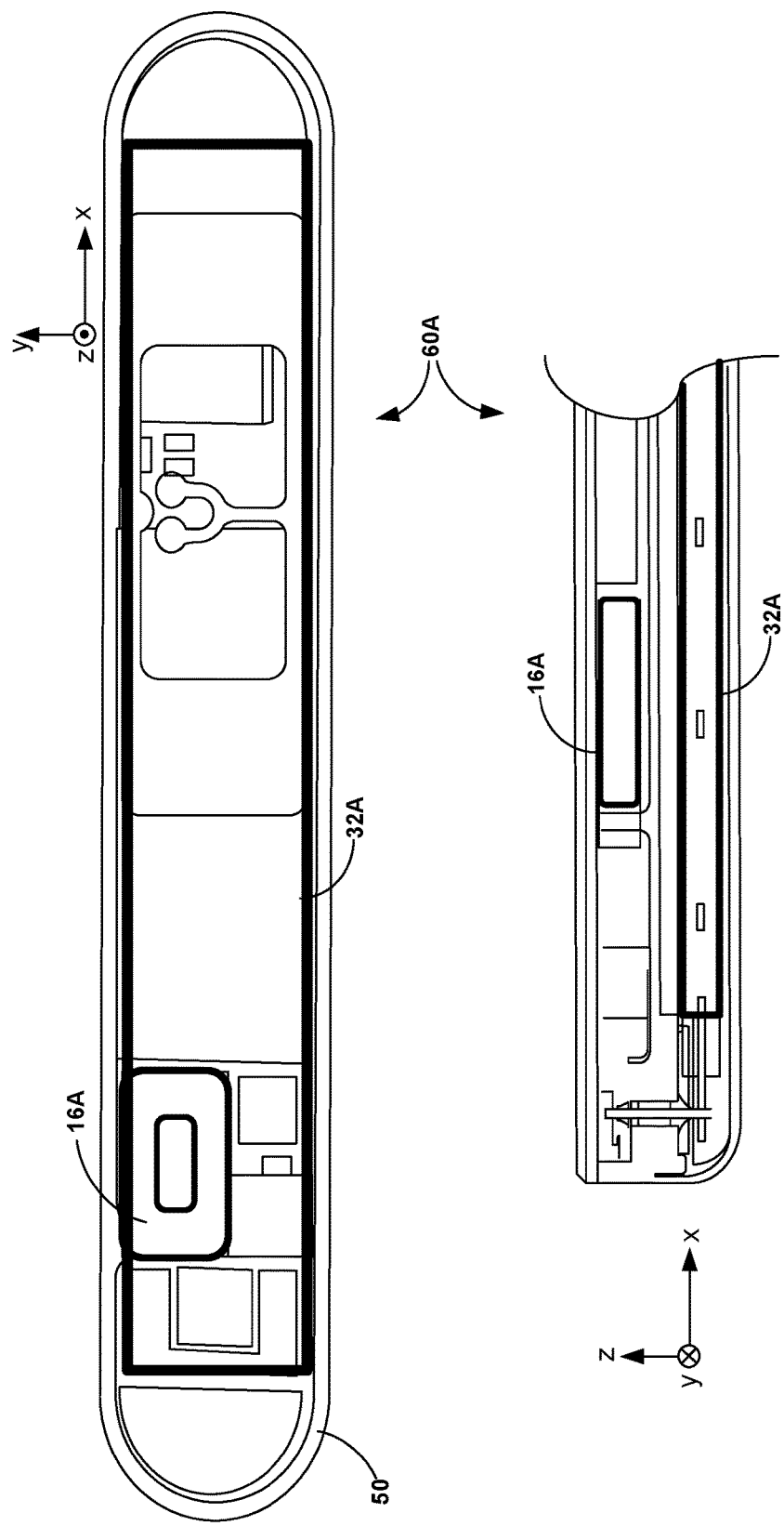
FIGS. 6A-6C each include a respective perspective and cross-sectional view, and each depict a respective one of three example arrangements of a receive coil and a rechargeable battery within an implantable medical device, according to some examples of this disclosure.
Figure 6B:
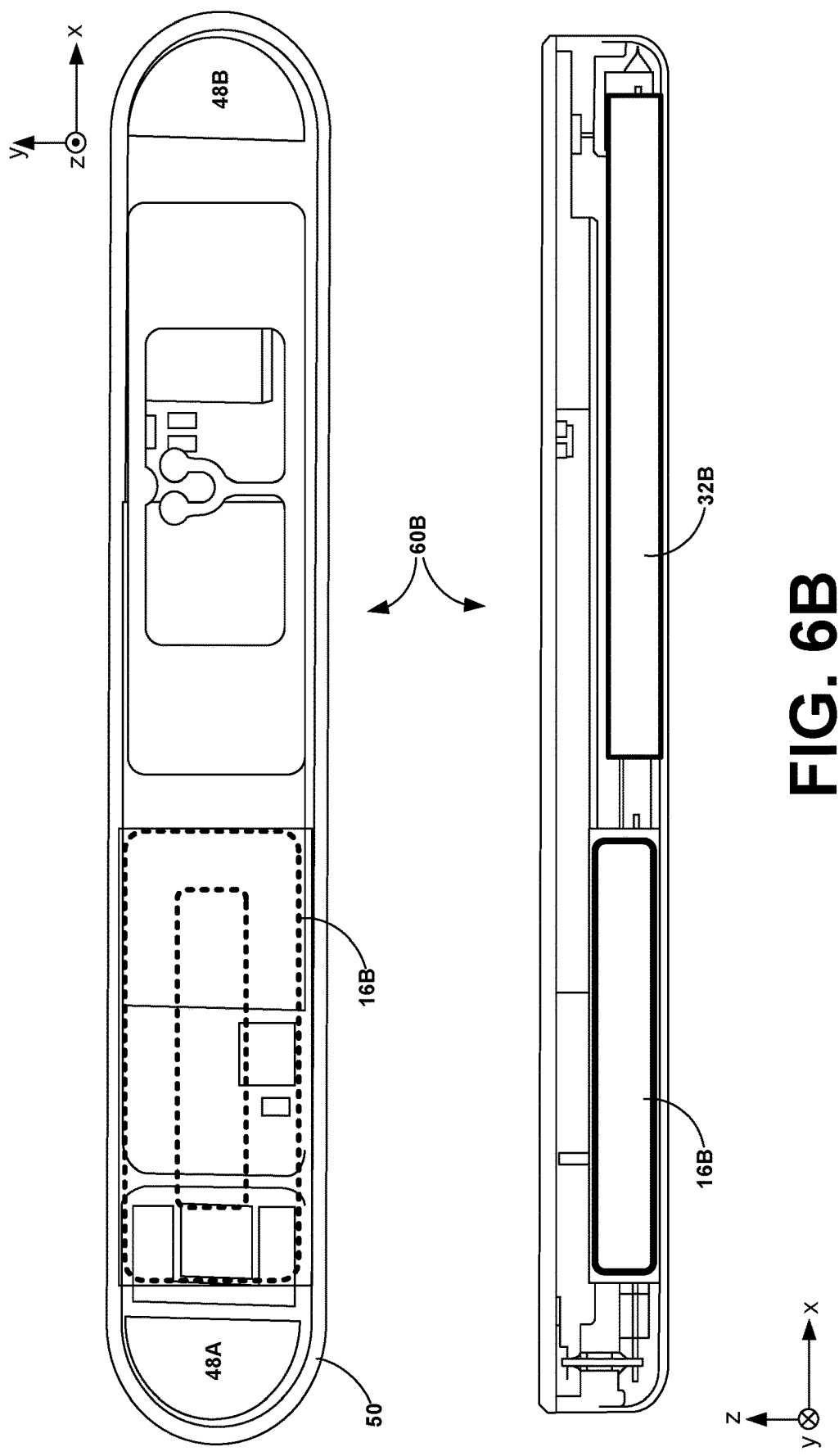
Figure 6C:
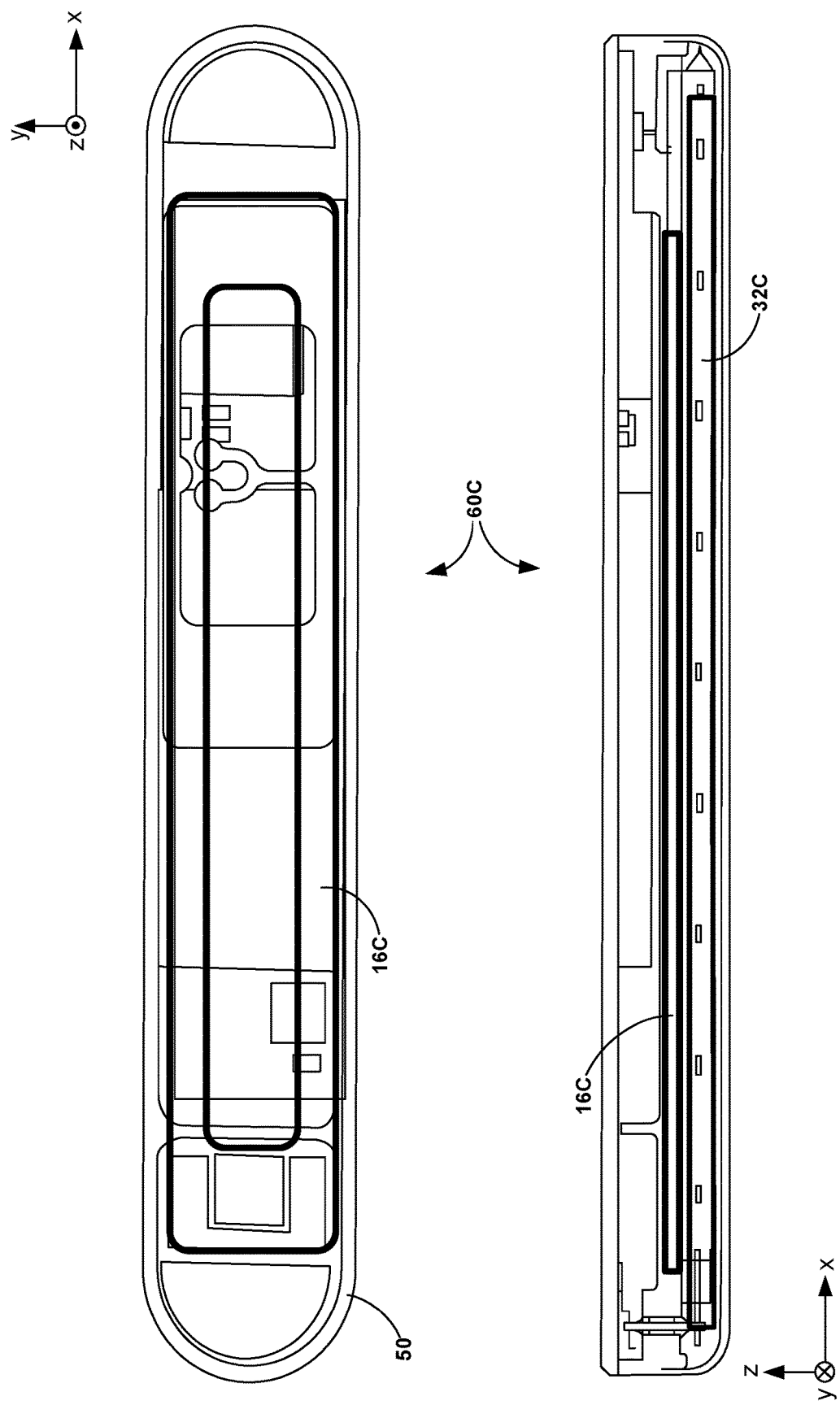

FIGS. 6A-6C depict three example configurations and arrangements 60A-60C of a planar receive coil 16A-16C, and a rechargeable battery 32A-32C within battery housing 50A-50C of an IMD. Different sizes, shapes, and arrangements of the coil and the battery may be selected to conform to space constraints within the internal volume of the enclosure formed by battery housings 50 and cover 52, and satisfy other performance parameters of the IMD. For example, a larger battery size may correspond to a larger battery capacity, allowing for IMD 14 to remain functional for longer periods of time in between recharges. Similarly, a larger coil size may be desirable to increase the speed of an individual recharging event (e.g., faster recharging). In some examples of IMD 14, configurations of the coil and the battery may be selected so as to achieve a "1-1-1" configuration, wherein the receive coil may charge the battery within one hour, and wherein the battery has a capacity allowing for one year in between recharges, with one year reserve capacity remaining in the battery at the time of each annual recharge (e.g., a total battery capacity providing for about two years of continuous use). It has been demonstrated that the two years of continuous use may be provided for a battery having a capacity of between about 45 and 60 milliampere-hours (mAh).

FIG. 6A depicts a first example arrangement 60A. In the example depicted in FIG. 6A, receive coil 16A includes a relatively small profile as measured along the x and y axes, so as to fit within a small compartment located near the top (as measured along the z-axis) of housing 50, e.g., between certain circuitry formed on cover 52. Some example dimensions of receive coil 16A include about 6 mm (along the x-axis) by 4 mm (along the y-axis) by 1.3 mm (along the z-axis).

Conversely, battery 32A includes a relatively large profile that extends nearly the entire length and width (as measured along the x and y axes, respectively) of device housing 50. The configuration depicted in FIG. 6A may exhibit a relatively a relatively longer battery life (e.g., useful lifespan duration in between required recharge events), due to the larger size of battery 32A. However, the configuration depicted in FIG. 6A may also exhibit a relatively longer recharge period, due to the relatively smaller receive coil 16A.

FIG. 6B depicts a second example arrangement 60B. In the example depicted in FIG. 6B, battery 32B has had its length (as measured along the x-axis) reduced by approximately half, as compared to battery 32A of FIG. 6A. Accordingly, receive coil 16B may be located below the plane in which circuitry formed on cover 52 is located along the z-axis, adjacent to battery 32B, and may include a relatively larger profile as measured along the x and y axes, so as to fit within the same space occupied by the other half of battery 32A of FIG. 6A. Some example dimensions of receive coil 16B include about 15 to 25 mm (along the x-axis) by 6.5 mm (along the y-axis) by 1.7 mm (along the z-axis). Configuration 60B depicted in FIG. 6B may exhibit a relatively a relatively shorter battery life, due to the smaller size of battery 32B as compared to battery 32A. However, the configuration depicted in FIG. 6B may also exhibit a relatively shorter recharge period, due to the relatively larger receive coil 16B as compared to antenna 16A.

FIG. 6C depicts a third example arrangement 60C. In the example depicted in FIG. 6C, battery 32C has had its height (as measured along the z-axis) reduced by approximately half, as compared to battery 32A of FIG. 6A. Accordingly, receive coil 16C includes a relatively larger profile as measured along the x and y axes, so as to fit within the same space occupied by the other half of battery 32A of FIG. 6A, e.g., in a plane between battery 32A and circuitry formed on cover 52. In configuration 60C, both antenna 16C and battery 32C extend across a majority of the length and width of housing 50, as measured along the x and y axes, respectively. For example, receive coil 16C may have example dimensions of about 33 mm (along the x-axis) by 7 mm (along the y-axis) by 0.4 mm (along the z-axis). Configuration 60C depicted in FIG. 6C may exhibit a relatively a relatively shorter battery life, due to the smaller size of battery 32C as compared to battery 32A. However, the configuration depicted in FIG. 6C may also exhibit a relatively shorter recharge period, due to the relatively larger receive coil 16C as compared to antenna 16A.

Figure 7A:
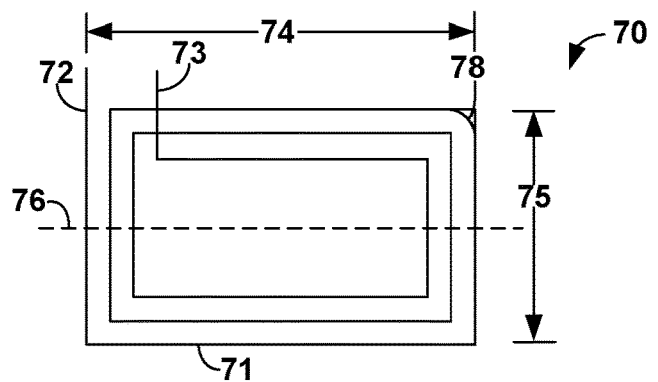
FIGS. 7A-7C depict three example configurations for a receive coil for a rechargeable implantable medical device, according to some examples of this disclosure.
Figure 7B:
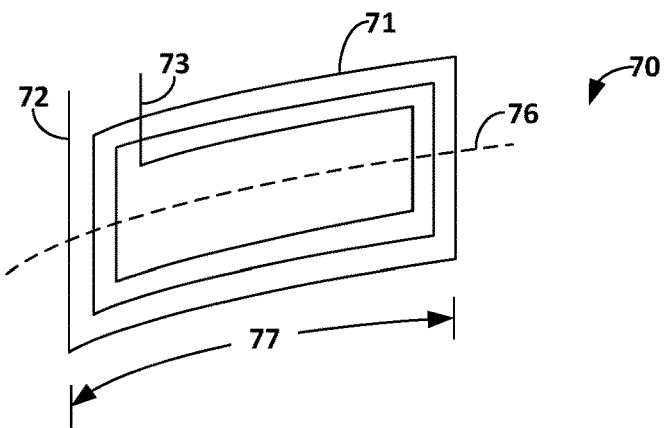
Figure 7C:
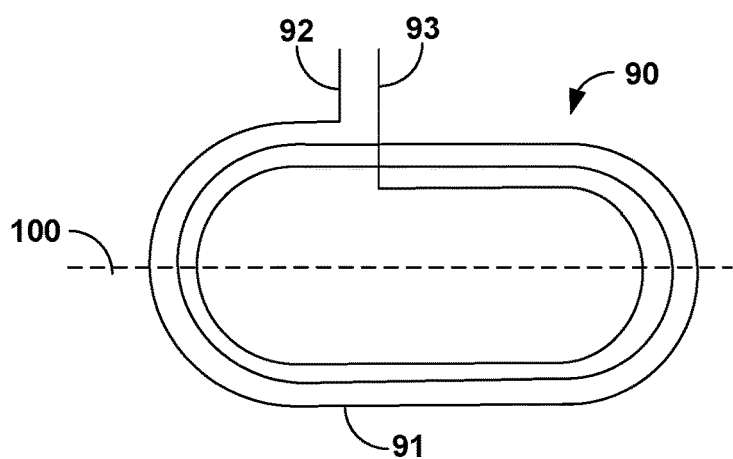

FIGS. 7A-7C depict three example electrical conductors configured to form a planar receive coils for a rechargeable IMD, according to some examples of this disclosure. As shown in FIG. 7A, an electrical conductor 71 is formed into a coil winding having a substantially rectangular shape. The outer-most winding of electrical conductor 71 extends along a length dimension 74, and along a width dimension 75. Length dimension 74 has a same orientation as an orientation of a longitudinal axis 76 extending across receive coil 70 parallel to the length dimension 74. A first end of electrical conductor 71 is electrically coupled to a first lead 72. A second end of electrical conductor 71 is electrically coupled to a second lead 73. First lead 72 and second lead 73 may extend to and electrically couple receive coil 70 with recharging circuitry of the implantable medical device, (not shown in FIG. 7A, but for example recharging circuitry 30 in FIG. 3), which allows currents induced into receive coil 70 by magnetic field(s) imposed onto receive coil 70 to be used to recharge a power source of the IMD coupled to the receive coil, or to power the operation of the electrical circuitry of the device.

As shown in FIG. 7A, the windings of receive coil 70 extending from first lead 72 form the outer-most winding of the receive coil, with additional windings being progressively formed within the previous winding as the electrical conductor 71 extends toward second lead 73. As such, the overall thickness dimension of the receive coil 70 (e.g., a thickness dimension of receive coil 70 orthogonal to both the length dimension 74 and the width dimension 75) may be the thickness of a diameter of the electrical conductor 71. In other words, the coil winding of receive coil 70 may be configured as a flat-wound coil having a generally rectangular shape in the length and width dimensions. Variations in the shape of the coil windings of electrical conductor 71 may include having the corners where the direction of the electrical conductor changes from a lengthwise to widthwise direction include a rounded or curved shape, as illustratively shown by corner radius 78. Further, the number of turns or windings included in receive coil 70 is not limited to a particular number of turns, and in some examples includes ten turns, wherein each turn includes a portion of the electrical conductor forming a four-sided winding of receive coil 70.

As shown in FIG. 7A, first lead 72 and second lead 73 are coupled to the electrical conductor 71 at a same corner of the coil winding, so that the first lead 72 and the second lead 73 extend from the coil winding in close proximity to one another. However, the positions of first lead 72 and second lead 73 are not limited to any particular arrangement, such as the arrangement as shown in FIG. 7A. In some examples leads 72 and 73 may extend from other positions of the coil winding of the receive coil 70, including having first lead 72 and second lead 73 extend from different portions of the coil windings so that these leads do not extend from portions of the receive coil that are in close proximity to one another.

Electrical conductor 71 is not limited to being formed from any particular type of material, and may be formed from a conductive metal, such as copper, that is easily formed into a wire and may be easily bent to form the desired shape of the coil winding used to form receive coil 70. The electrical conductor used to form receive coil 70 in some examples may include an insulative material, such as enamel, that is coated over the exterior surface of the conductor to provide an insulative layer between the individual coil windings. In various examples, the electrical conductor used to form receive coil 70 is a multi-strand conductor, such as Litz wire, wherein the electrical conductor used to form each winding is insulated along the outer surface of the electrical conductor, for example using a coating, such as enamel, to reduce the skin effect of the electrical conductor. Skin effect is the characteristic of electrical current flowing through an electrical conductor that causes the flow of current in the electrical conductor to travel though the outer portion, e.g., the "skin" of the conductor, and not through the inner portion of the electrical conductor. The skin effect is more pronounced at higher frequencies. The use of Litz wire may help reduce the skin effect in the electrical conductor at higher frequencies.

An example of receive coil 70 may be retained in the flat-wound configuration as shown in FIG. 7A and used as a receive coil in an implantable medical device, for example as receive coil 16 of IMD 14 as illustrated and described with respect to FIGS. 1-6C. In other examples, receive coil 70 may be formed into a curved shape, as illustrated in FIG. 7B. When formed into a curved shape, receive coil 70 may or may not be affixed to a ferrite sheet.

As illustrated in FIG. 7A, in some examples an outermost loop of receive coil 70 may be bent so as to form a rounded corner 78. For example, receive coil 70 may include one or more rounded corners 78 so as to conform to a shape of an interior volume of battery housing 50 (FIGS. 6A-6C), such as a bathtub-shaped housing 50. In some examples, a rounded coil (e.g., a coil having rounded corners 78) may perform better mechanically than a rectangular coil having sharp-angled corners.

As illustrated in FIG. 7B, in some examples, receive coil 70 may be bent or curved along central longitudinal axis 76. In examples where the receive coil 70 is affixed to a ferrite sheet (such as ferrite sheet 54 as illustrated and described with respect to FIG. 5), the amount of curvature of the receive coil 70 may be formed so that receive coil 70 may be affixed to a curved surface of the ferrite sheet. In examples where receive coil 70 is not affixed to a ferrite sheet, receive coil 70 may be bent along the length of longitudinal axis 76 as shown in FIG. 7B. For example, receive coil 70 may be bent so as to conform to a curved inner surface of battery housing 50 of IMD 14.

FIG. 7C illustrates an electrical conductor 91 configured to form a receive coil 90 for an IMD according to various examples described in this disclosure. As shown in FIG. 7C, an electrical conductor 91 is formed into a coil winding having a circular or oval shape. A first end of electrical conductor 91 is electrically coupled to a first lead 92 and a second end of electrical conductor 91 is electrically coupled to a second lead 93. First lead 92 and second lead 93 may be configured to extend to and electrically couple receive coil 90 with recharging circuitry of an implantable medical device (not shown in FIG. 7C, but for example recharging circuitry 30 in FIG. 3), which allows currents induced into receive coil 90 by magnetic field(s) imposed onto receive coil 90 to be used to recharge a power source of an implanted medical device coupled to the receive coil, or to power the operation of the electrical circuitry of the device.

As shown in FIG. 7C, the windings of receive coil 90 extending from first lead 92 forms the outer-most winding of the receive coil, with additional windings being progressively formed within the previous windings as the electrical conductor 91 extends toward second lead 93. As such, the overall thickness dimension of the receive coil 90 (e.g., a thickness dimension of receive coil 90) may be the thickness of the diameter of the electrical conductor 91. In other words, the coil winding of receive coil 90 as shown in FIG. 7C may be configured as a flat-wound planar coil having a generally circular or oval shape. The number of turns or windings included in receive coil 90 is not limited to a particular number of turns, and in some examples includes ten turns, wherein each turn includes a portion of the electrical conductor forming a generally circular or oval shaped winding of the receive coil.

As shown in FIG. 7C, first lead 92 and second lead 93 are coupled to the electrical conductor 91 at a same relative position of the respective coil winding the to which these leads are attached, so that the first lead 92 and the second lead 93 extend from the coil winding in close proximity to one another. However, the positions of first lead 92 and second lead 93 are not limited to any particular arrangement, such as the arrangement as shown in FIG. 7C. In some examples leads 92 and 93 may extend from other positions of the coil winding of the receive coil 90, including having first lead 92 and second lead 93 extend from different portions of the coil windings so that these leads do not extend from portions of the receive coil that are in close proximity to one another.

Electrical conductor 91 is not limited to being formed from any particular type of material, and may be formed from any type of electrical conductor described above with respect to electrical conductor 71, including a conductive metal, such as copper, that is easily formed into a wire and may be easily bent to form the desired shape of the coil winding used to form receive coil 70. The electrical conductor used to form receive coil 90 in FIG. 7C in some examples may include an insulative material, such as enamel, coated over the exterior surface of the conductor to provide an insulative layer between the individual coil windings. In various examples, the electrical conductor used to form receive coil 90 is a multi-strand conductor, such as Litz wire, wherein the electrical conductor used to form each winding is insulated along the outer surface of the electrical conductor, for example using a coating, such as enamel, to reduce the skin effect of the electrical conductor.

Figure 8:
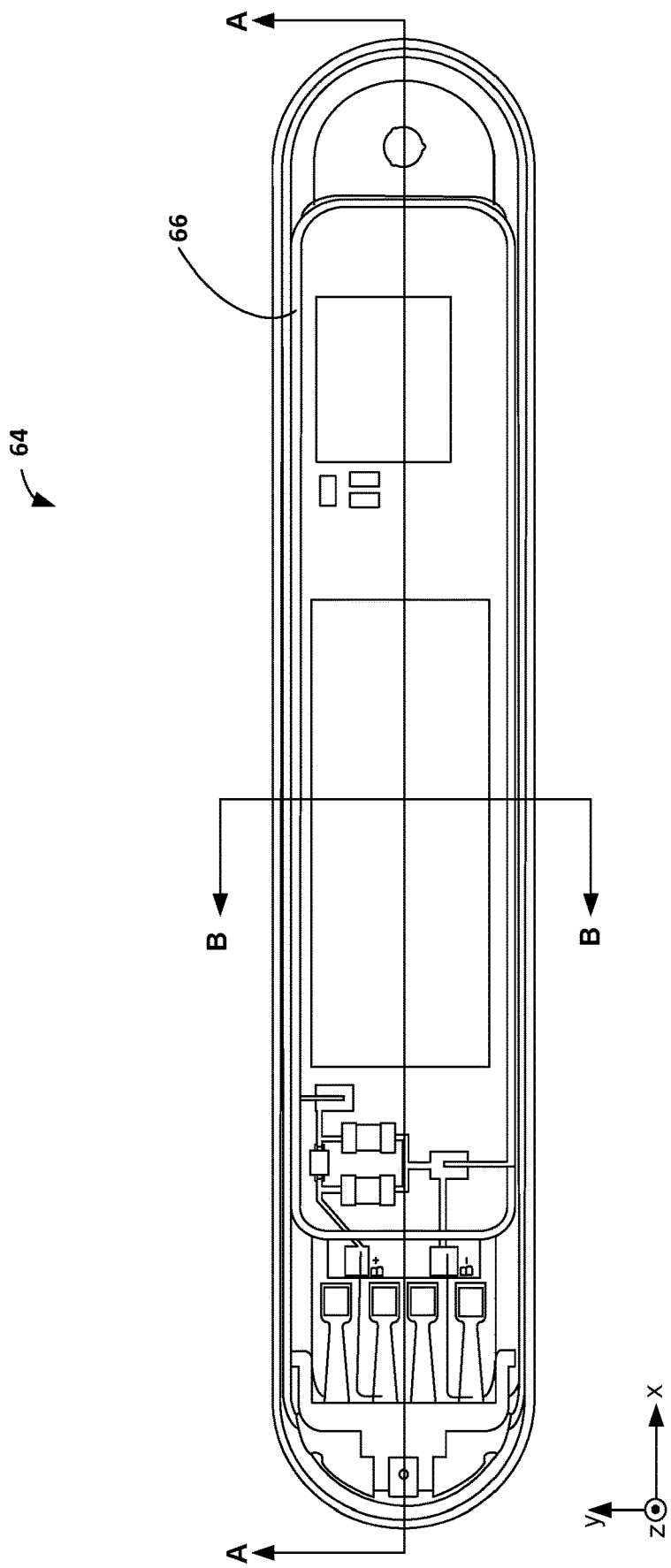
FIG. 8 is an overhead view of an example rechargeable IMD having a tubular receive coil, according to some examples of this disclosure.

FIG. 8 is an overhead view of another example rechargeable IMD 64, according to some examples of this disclosure. In the example depicted in FIG. 8, IMD 64 includes a tubular receive coil 66, rather than a planar coil 16 as depicted in previous examples. As depicted further in FIGS. 9A and 9B, tubular coil 66 includes a plurality of coil loops or turns, each coil loop having a same shape and circumference as every other coil loop, wherein consecutive coil loops are stacked on top of one another, as measured along the z-axis in FIG. 8.

Figure 9A:
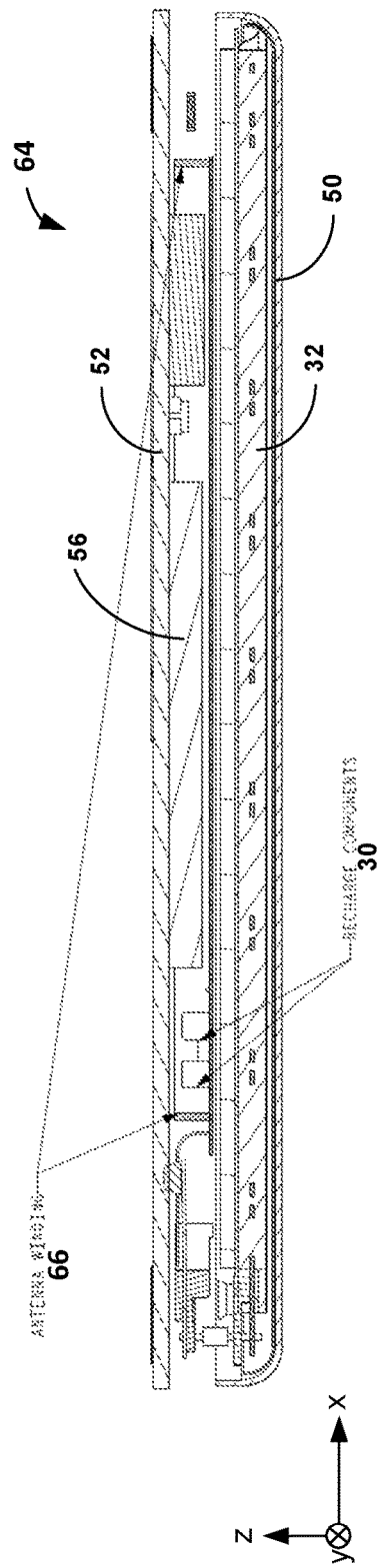
FIGS. 9A and 9B are cross-sectional views of the example rechargeable IMD of FIG. 8.
Figure 9B:
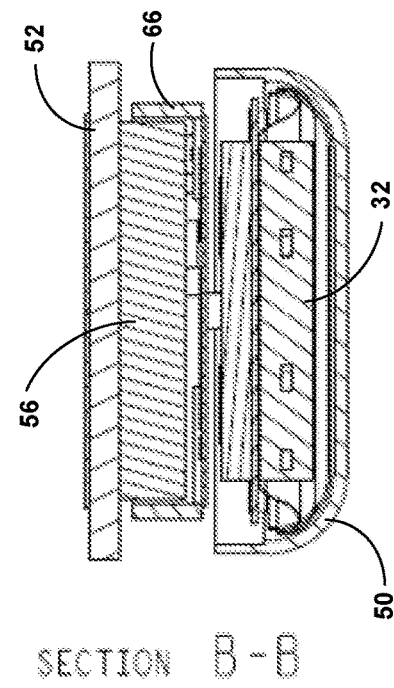

FIG. 9A is a cross-sectional view of the example rechargeable IMD 64 of FIG. 8, as viewed along line A-A. FIG. 9B is a cross-sectional view of the example rechargeable IMD 64 of FIG. 8, as viewed along line B-B. As shown in FIGS. 9A and 9B, the stacked coil windings of tubular antenna 66 create a rectangular, tubular shell extending upward along the z-axis. The rectangular shell defines an internal volume of space into which control circuitry 56, which may be coupled to an underside of sapphire cover 52, may fit when cover 52 is sealingly coupled onto housing 50.

Figure 10A:
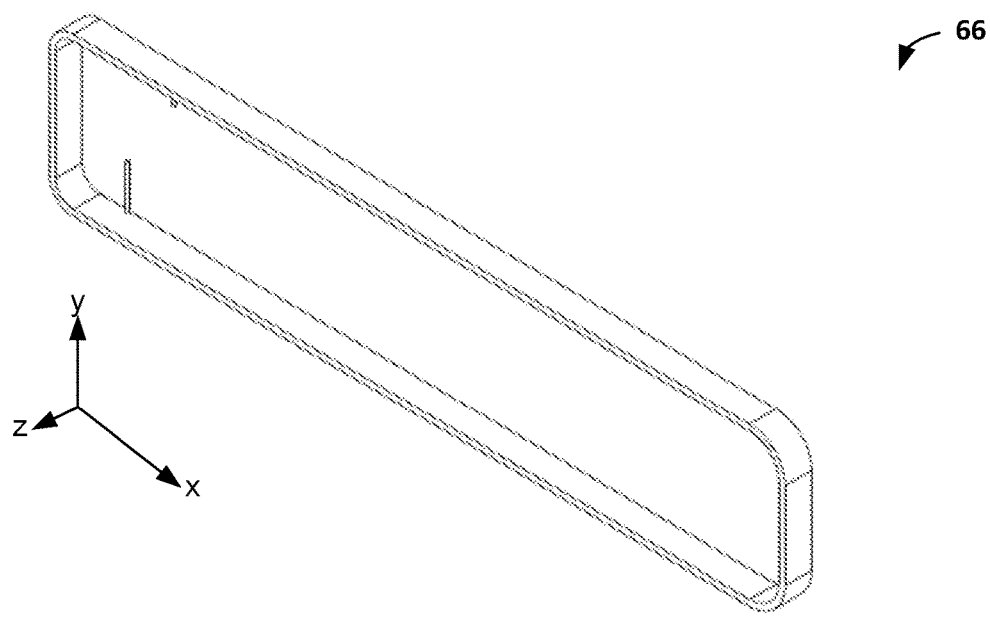
FIG. 10A is an oblique view and FIG. 10B is a plan view of an example tubular receive coil for a rechargeable IMD, according to some examples of this disclosure.
Figure 10B:
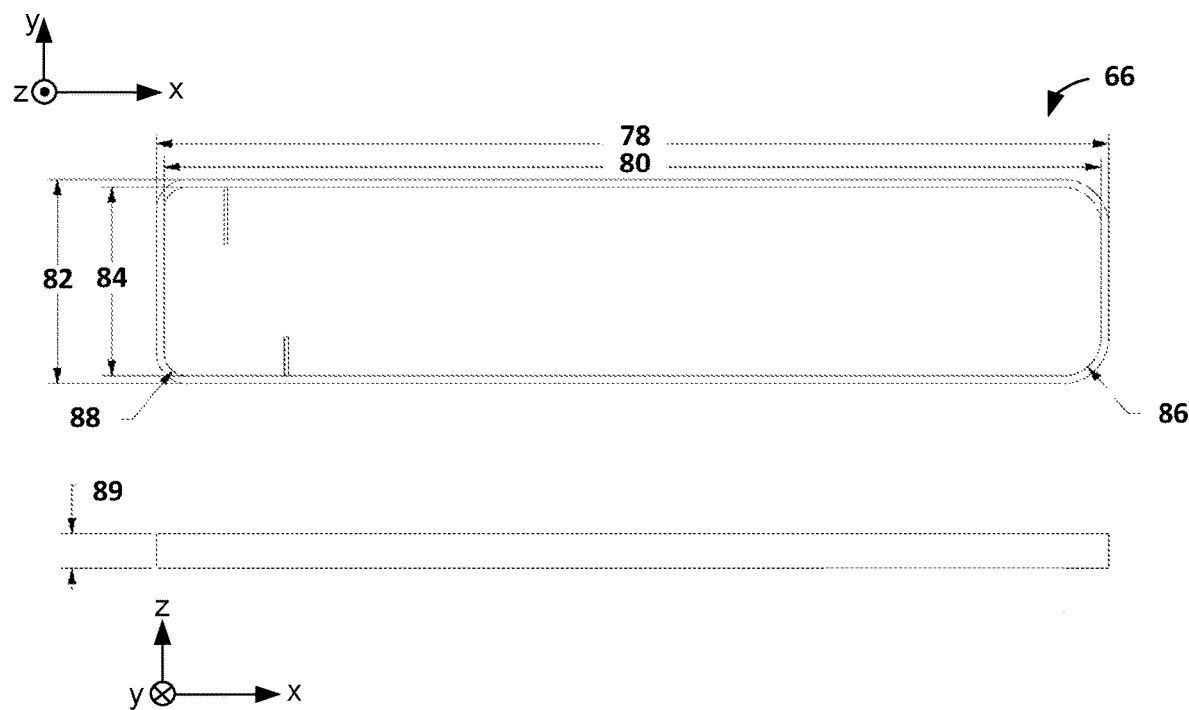

FIG. 10A is an oblique view and FIG. 10B is a plan view of the example tubular receive coil 66 of FIG. 8. Specifically, FIGS. 10A and 10B depict some example dimensions of tubular antenna 66. For example, tubular antenna 66 may include between about 20 and 40 coil turns of a wire, such as 36-gauge magnet wire. The coils may form a generally rectangular tube defining an outer length 78 of about 1.22 to 1.26 inches, as measured along the x-axis; an inner length 80 of about 1.20 to 1.24 inches, as measured along the x-axis; an outer width 82 of about 0.264 to 0.268 inches, as measured along the y-axis; an inner width 84 of about 0.244 to 0.248 inches, as measured along the y-axis; a first inner radius of curvature 86 of about 0.048 to 0.052 inches; a second inner radius of curvature 88 of about 0.028 to 0.032 inches; and a height 89 of about 0.043 to 0.047 inches, as measured along the z-axis.

Figure 11:
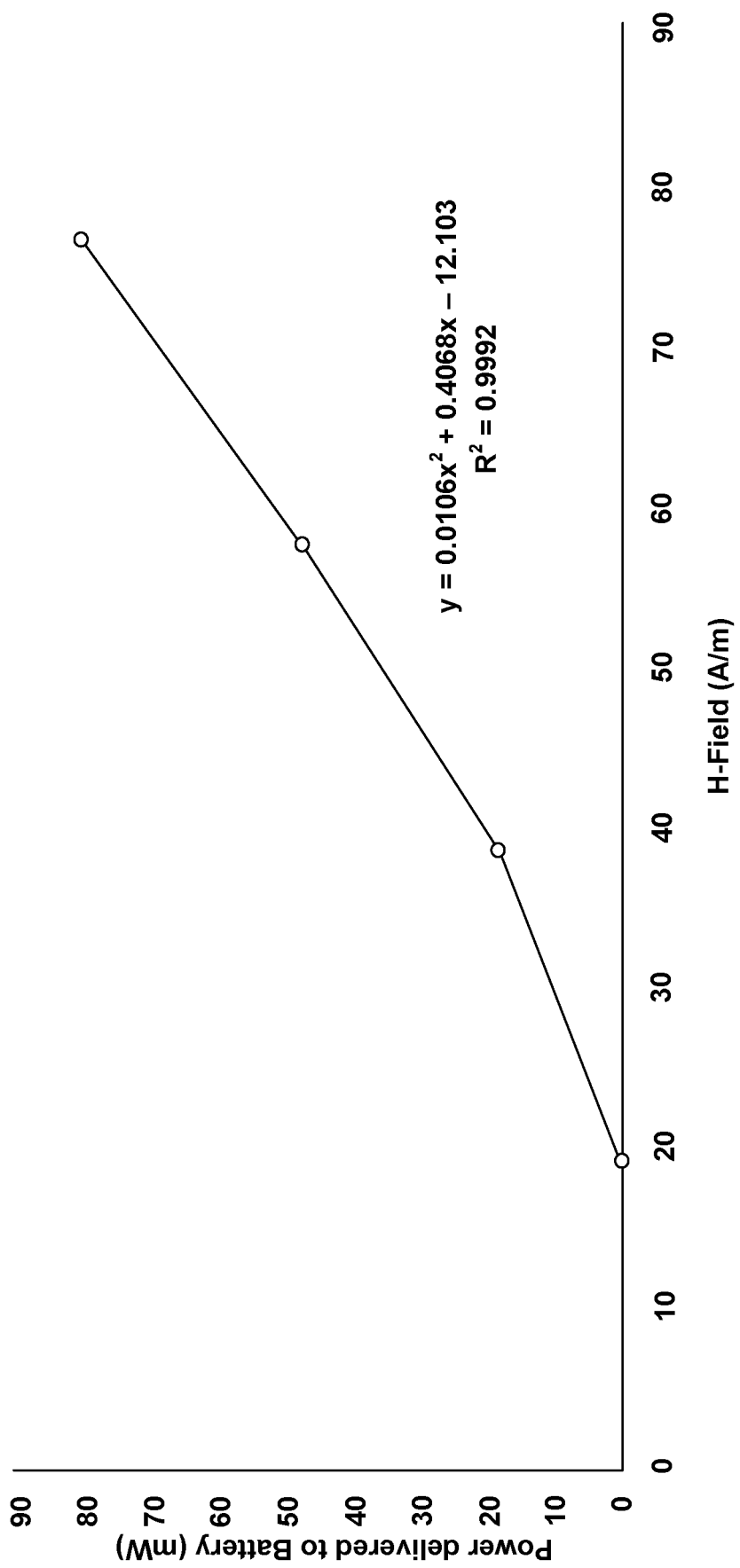
FIG. 11 is a line graph depicting an example mathematical relationship between a magnetic field strength and an amount of power delivered to a rechargeable battery, according to some examples of this disclosure.

FIG. 11 is a line graph depicting an example mathematical relationship between a magnetic field strength and an amount of power delivered to a rechargeable battery, according to some examples of this disclosure. As shown in FIG. 11, there is an approximately linear relationship between applied magnetic field 26 (FIG. 2) and the power delivered to the rechargeable battery 32 (FIG. 3). Accordingly, faster recharging times may be achieved by applying a stronger magnetic field to receive coil 16. However, higher power transfers may additionally correspond to the generation of waste heat, which may need to be kept below threshold levels so as to avoid uncomfortable heating of IMD 14 when implanted within a patient 12.

Figure 12:
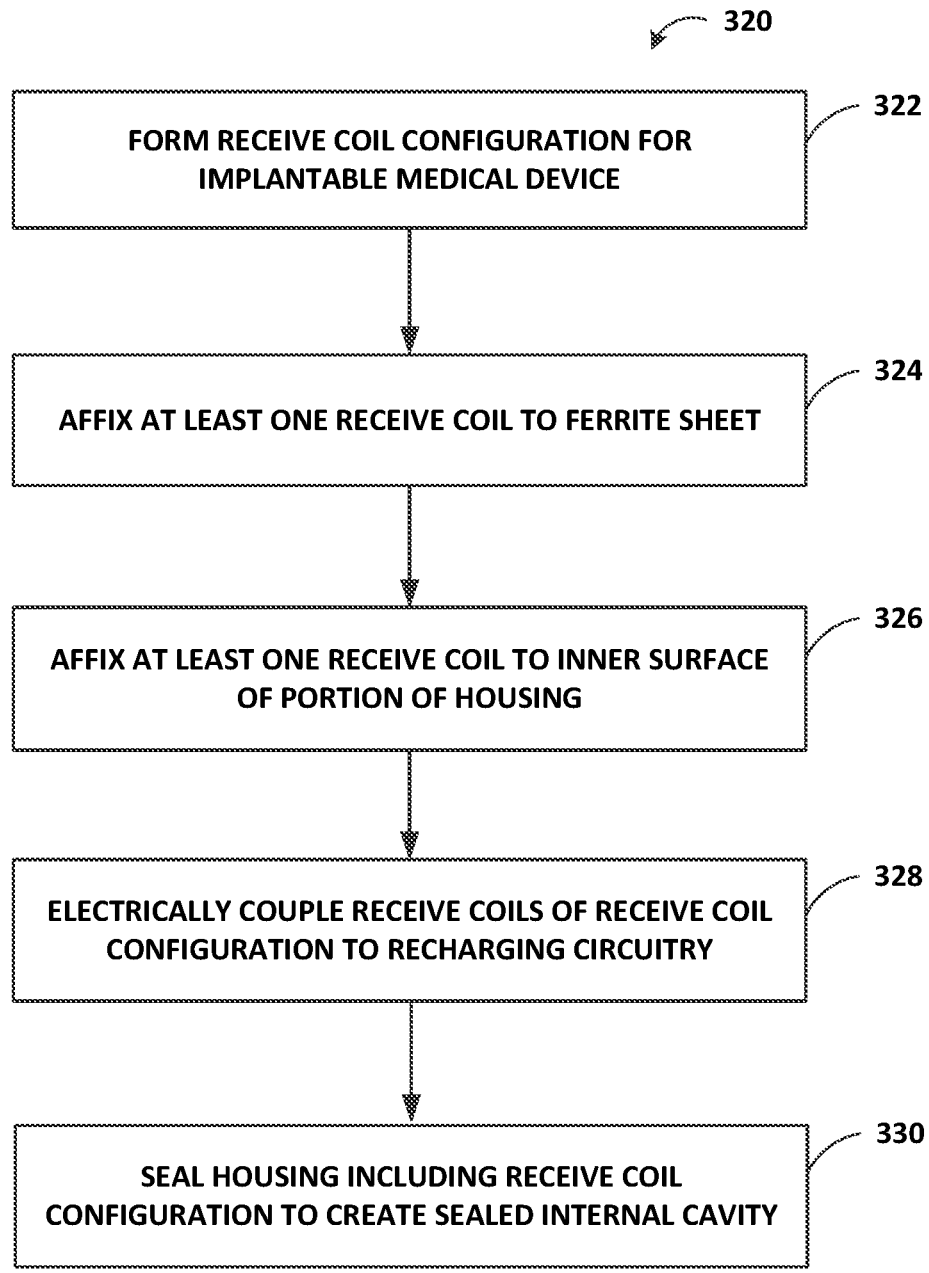
FIG. 12 is a flowchart illustrating an example method according to various examples described in this disclosure.

FIG. 12 is a flowchart illustrating an example method according to various examples described in this disclosure. Method 320 includes a method for manufacturing a receive coil configuration for an IMD that is to be implanted within a patient according to the devices, systems, and techniques described herein. Method 320 is described as manufacturing a receive coil configuration for an IMD 14 (FIG. 1) designed to be implanted within a patient, and to include a receive coil configuration configured to generate a recharging current when a magnetic field is imposed on the antenna, the recharging current for recharging a power source (e.g., battery 32) of the device 14. However, method 320 is not limited to manufacturing the implantable medical device 14 having the receive coil configuration as illustrated and described, and may be applied to the manufacturing process of a variety of IMDs having a receive coil configuration according to the examples as described throughout this disclosure, and any equivalents thereof.

Method 320 includes forming a receive coil configuration for an IMD 14 (block 322). The receive coil may include a coil winding formed from an electrical conductor as a spiral-wound planar coil, such as receive coil 90 as illustrated and described with respect to FIGS. 7A-7C, or as a tubular coil, such as receive coil 66 as illustrated and described with respect to FIGS. 10A-10B.

The electrical conductor used to form the coil winding of the receive coils is not limited to any particular type of electrical conductor, and may be any type of electrical conductor that can be utilized to form the receive coils as described throughout this disclosure, including a wire comprising from a conductive metal such as copper, or a multi-strand electrical conductor such as Litz wire. The coil winding may be formed using any techniques that may be utilized to form the receive coils, including any of the technique as described throughout this disclosure.

Referring again to FIG. 12, method 320 includes affixing at least one receive coil of the antenna configuration to an inner surface of a portion of the housing 50 of IMD 14 (block 326). In some examples, the portion of the housing including the inner surface is distinct from a separate cover portion 52. Affixing the at least one receive coil to the inner surface of the housing 50 may include affixing the at least one receive coil directly to the inner surface so that the coil winding forming the at least one receive coil are in contact with at least some portion of the inner surface. Affixing the at least one receive coil to the inner surface of the housing may include affixing the at least one receive coil to a first surface of a flexible ferrite sheet 54 (block 324), and then affixing a second surface of the ferrite sheet 54 opposite the first surface to the inner surface of the housing so that the ferrite sheet is positioned between the inner surface and the coil windings of the at least one receive coil (block 326).

Affixing the at least one receive coil to the inner surface of the housing may include affixing a plurality of receive coil windings directly to the inner surface of the housing 50 (e.g., without the intervening ferrite sheet 54). In some examples, the plurality of receive coils includes a plurality of flat spiral-wound coils forming a planar antenna. In some examples, the plurality of receive coils includes a plurality of stacked coils forming a tubular antenna. Affixing the at least one receive coil to the inner surface of the housing may include positioning a second receive coil within the interior cavity that is at least partially enclosed by the inner surface.

Method 320 includes electrically coupling the receive coil or coils of the receive coil configuration to a recharging circuitry 30 of the device 14 (block 328). Coupling the receive coil configuration may include coupling a first lead of each receive coil to an individual diode, and coupling a second lead of each receive coil to a common voltage conductor. In examples of the receive coil configuration that include a plurality of receive coils, coupling the receive coil configuration to the recharging circuitry 30 may include coupling each receive coil to electrical circuitry, including electrical diodes, so that any electrical currents generated in any of the receive coils can be summed together to generate a recharging current comprising the total of the electrical current(s) being generated by any and all of the receive coils at any given time.

Method 320 includes coupling the portion of the housing 50 including the receive coil configuration with one or more additional portions of the housing of the implantable medical device (block 330). Coupling the portion of the housing including the receive coil configuration with additional portions of the housing may include coupling a cover 52 with a housing portion 50. In some examples, method 320 may include forming control circuitry, configured to control one or more functions of IMD 14, to the inner surface of cover 52 prior to coupling cover 52 to the rest of housing 50. Method 320 includes sealing the portion of the housing to the cover 52 to create a sealed internal cavity that includes the receive coil configuration. Coupling the housing 50 with cover 52 may include forming a sealed seam between a bottom side of the cover 52 with housing portion 50 of the IMD 14. Sealing the portion of the housing and/or the antenna window may include the use of any materials, such as adhesives, and or any type of welding or bonding process that may be used to provide a hermetic seal between the type of material used to form the portion of the housing and the type of material used to form the cover 52.

Use of the devices, systems, and techniques described in this disclosure are not limited to use in devices only during recharging sessions applied to the devices. An example of a receive coil configuration as described throughout this disclosure, or any equivalent thereof, may be included a part of a passive device. In some examples, the passive device may not include an internal power source capable of storing electrical energy for extended periods of time during which the device may be required to operate, wherein the device may only operate when and during a time or over time periods when the device is being energized from an external power source, for example by receiving power from an external device through inductively coupled electrical energy provided by the external device. When operating a passive device, an external device that may include an external recharge coil arranged to be electrically energized to generate a magnetic field that is imposed on the receive coil configuration incorporated within or coupled to the passive device. The imposed magnetic field generates one or more currents in the receive coil configuration of the passive device, and additional circuitry of the passive device is arranged to receive these induced currents to electrically power and operate the passive device. These current(s) inducted into the receive coil configuration may be referred to as "operating current" because they are used to electrically power and operate the passive implantable medical device.

Once powered by the induced currents, the IMD may perform a variety of functions, including sensing physiological parameter associated with a patient in order to monitoring and/or diagnose a condition of the patient, and/or to provide therapy, such as electrical stimulation therapy, to the patient while the passive device is being powered through the imposed magnetic field. The need to operate the passive device in some instances may only require that the device be powered for a short interval of time, for example for a thirty-minute time period and only periodically, for example once daily, or in other examples one time per week or once monthly. By eliminating the need to have a power source located within or as part of the passive device, the overall size and/or the dimension of the passive device may be reduced relative to a similar device that includes a power source included as part of the device. The smaller size for the passive device may allow a less intrusive implantation to implant the passive device at the implantation site, and may contribute to patient comfort following implantation of the device due to the smaller size of the implanted device.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processor circuitry," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random-access memory (RAM), read-only memory (ROM), non-volatile random-access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various aspects of this disclosure have been described. These and other aspects are within the scope of the following claims.

What is claimed is:

1. An implantable medical device comprising:
   a rechargeable battery comprising a battery housing;
   a non-metallic substrate attached to the battery housing, wherein the non-metallic substrate and the battery housing form an outer housing of the implantable medical device;
   control circuitry formed on the non-metallic substrate and located within the outer housing of the implantable medical device, wherein the control circuitry is configured to control functioning of the implantable medical device;
   a receive coil within the outer housing of the implantable medical device, wherein the receive coil is configured to receive energy from outside of the outer housing of the implantable medical device, and wherein the receive coil defines an inner space in which the control circuitry is disposed when the non-metallic substrate is attached to the battery housing; and
   recharge circuitry within the outer housing of the implantable medical device and coupled to the receive coil, the recharge circuitry configured to receive the energy from the receive coil, and recharge the rechargeable battery using the received energy.

2. The implantable medical device of claim 1, wherein the implantable medical device comprises a cardiac monitor, and the control circuitry is configured to monitor at least one cardiac parameter of a patient.

3. The implantable medical device of claim 1, wherein the non-metallic substrate comprises sapphire.

4. The implantable medical device of claim 1, wherein the rechargeable battery extends a majority of a length and a width of the outer housing, and wherein the receive coil is disposed between the battery housing and the non-metallic substrate.

5. The implantable medical device of claim 4, wherein the receive coil comprises dimensions of about 6 mm by 4 mm by 1.3 mm.

6. The implantable medical device of claim 4, wherein the receive coil extends a majority of the length and the width of the outer housing.

7. The implantable medical device of claim 6, wherein the receive coil comprises dimensions of about 33 mm by 7 mm by 0.4 mm.

8. The implantable medical device of claim 1, wherein the receive coil and the rechargeable battery each extend a respective portion of a length of the outer housing, and wherein the receive coil and the rechargeable battery are approximately coplanar.

9. The implantable medical device of claim 1, wherein the receive coil comprises dimensions of about 1.7 mm by 6.5 mm by between 15 mm and 25 mm.

10. The implantable medical device of claim 9, wherein the receive coil is curved to conform to an inner surface of the battery housing.

11. The implantable medical device of claim 1, wherein the receive coil is affixed to a ferrite sheet.

12. The implantable medical device of claim 11, wherein the ferrite sheet is formed of a flexible material.

13. The implantable medical device of claim 1, wherein the receive coil comprises a spiral-wound planar coil.

14. The implantable medical device of claim 1, wherein the receive coil comprises a spiral-wound tubular coil.

15. A system for recharging a rechargeable battery located in an implanted medical device implanted in a patient, the system comprising:
   an electrical power source;
   at least one external recharging coil coupled to the electrical power source and configured to generate a magnetic field having a magnetic field direction when electrically energized by the electrical power source; and
   an implantable medical device comprising:
      a rechargeable battery comprising a battery housing;
      a non-metallic substrate attached to the battery housing, wherein the non-metallic substrate and the battery housing form an outer housing of the implantable medical device;
      control circuitry formed on the non-metallic substrate and located within the outer housing of the implantable medical device, wherein the control circuitry is configured to control functioning of the implantable medical device;
      a receive coil within the outer housing of the implantable medical device, wherein the receive coil is configured to receive energy from the at least one external recharging coil outside of the outer housing of the implantable medical device, and wherein the receive coil defines an inner space in which the control circuitry is disposed when the non-metallic substrate is attached to the battery housing; and
      recharge circuitry within the outer housing of the implantable medical device and coupled to the receive coil, the recharge circuitry configured to receive the energy from the receive coil, and recharge the rechargeable battery using the received energy.

16. The system of claim 15, wherein the implantable medical device comprises a cardiac monitor, and wherein the control circuitry is configured to monitor at least one cardiac parameter of a patient.

17. A method for manufacturing a rechargeable implantable medical device, the method comprising:
   positioning a receive coil on an outer surface of a battery housing of the implantable medical device;
   electrically couple the receive coil to a recharging circuitry of the implantable medical device;
   forming control circuitry onto a non-metallic substrate; and
   sealing the non-metallic substrate to the housing to enclose the receive coil, the recharging circuitry, and the control circuitry within the housing of the implantable medical device, wherein the receive coil defines an inner space in which the control circuitry is disposed when the non-metallic substrate is sealed to the battery housing.

18. The method of claim 17, further comprising
affixing the receive coil to a ferrite sheet; and
affixing the ferrite sheet including the at least one receive coil to the surface of the battery housing that the ferrite sheet is positioned between the receive coil and the surface.

19. The method of claim 18, wherein the implantable medical device comprises a cardiac monitor, and wherein the control circuitry is configured to monitor at least one cardiac parameter of a patient.

* * * * *